(12) United States Patent
Nakamura et al.

(10) Patent No.: US 7,724,428 B2
(45) Date of Patent: May 25, 2010

(54) OPERATING MICROSCOPE HAVING AN ARM FRAME

(75) Inventors: Motokazu Nakamura, Tokyo (JP);
Junichi Nozawa, Tokyo (JP)

(73) Assignee: Olympus Corporation (JP)

( * ) Notice: Subject to any disclaimer, the term of this patent is extended or adjusted under 35 U.S.C. 154(b) by 476 days.

(21) Appl. No.: 11/514,455

(22) Filed: Sep. 1, 2006

(65) Prior Publication Data

US 2006/0291045 A1   Dec. 28, 2006

Related U.S. Application Data

(63) Continuation of application No. PCT/JP2005/000602, filed on Jan. 19, 2005.

(30) Foreign Application Priority Data

Mar. 3, 2004   (JP) .............................. 2004-059811

(51) Int. Cl.
*G02B 21/00* (2006.01)

(52) U.S. Cl. .................. 359/384; 600/102; 248/123.11; 248/648

(58) Field of Classification Search ........................ None
See application file for complete search history.

(56) References Cited

U.S. PATENT DOCUMENTS 5,651,718 A * 7/1997 Nakamura ............... 248/123.2

FOREIGN PATENT DOCUMENTS

| EP | 1 251 380 A2 | 10/2002 |
|---|---|---|
| JP | 57-86806 | 5/1982 |
| JP | 59-154219 | 9/1984 |
| JP | 7-16239 | 1/1995 |
| JP | 7-184928 | 7/1995 |
| JP | 2001-112777 | 4/2001 |
| JP | 2002-165804 | 6/2002 |

OTHER PUBLICATIONS

International Preliminary Report with cited references for PCT Appln. No. PCT/JP2005/000602 dated Dec. 14, 2006.
International Search Report issued by PCT Office on Apr. 19, 2005 in connection with corresponding application No. PCT/JP2005/000602.
Information Sheet for IDS Under Rule 1.56 prepared by applicant for art disclosed in the instant specification.

(Continued)

*Primary Examiner*—Arnel C Lavarias
(74) *Attorney, Agent, or Firm*—Ostrolenk Faber LLP

(57) ABSTRACT

An operating microscope includes a base set on a floor surface, a post held for rotation around a vertical rotation axis with respect to the base, a horizontal motion arm held for rotation around a first horizontal rotation axis with respect to the post, a vertical motion arm held for rotation around a second horizontal rotation axis with respect to the horizontal motion arm, a lens barrel portion supported by the vertical motion arm, an elastic member which is provided between the post and the horizontal motion arm and cancels an angular moment around the horizontal motion arm, a fulcrum which is provided on the horizontal motion arm and receives a force from the elastic member, and a fulcrum moving mechanism configured to shift the position of the fulcrum in a direction substantially perpendicular to a longitudinal direction of the horizontal motion arm.

7 Claims, 21 Drawing Sheets

OTHER PUBLICATIONS

Office Action issued by the Japanese Patent Office on Nov. 24, 2009 in connection with corresponding Japanese Patent Application No. 2004-059811.

Translation of Office Action issued by the Japanese Patent Office on Nov. 24, 2009 in connection with corresponding Japanese Patent Application No. 2004-059811.

* cited by examiner

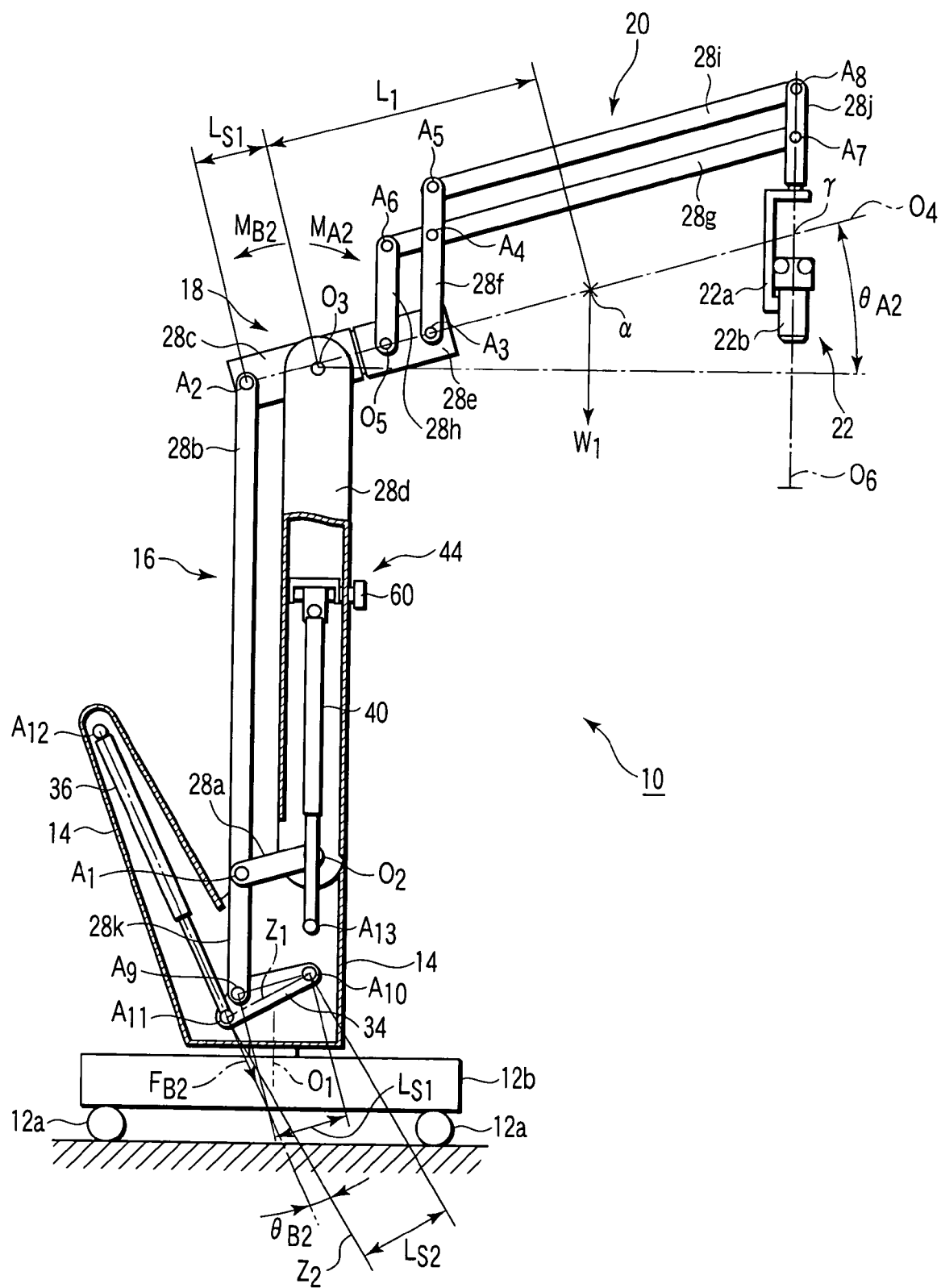
F I G. 2A

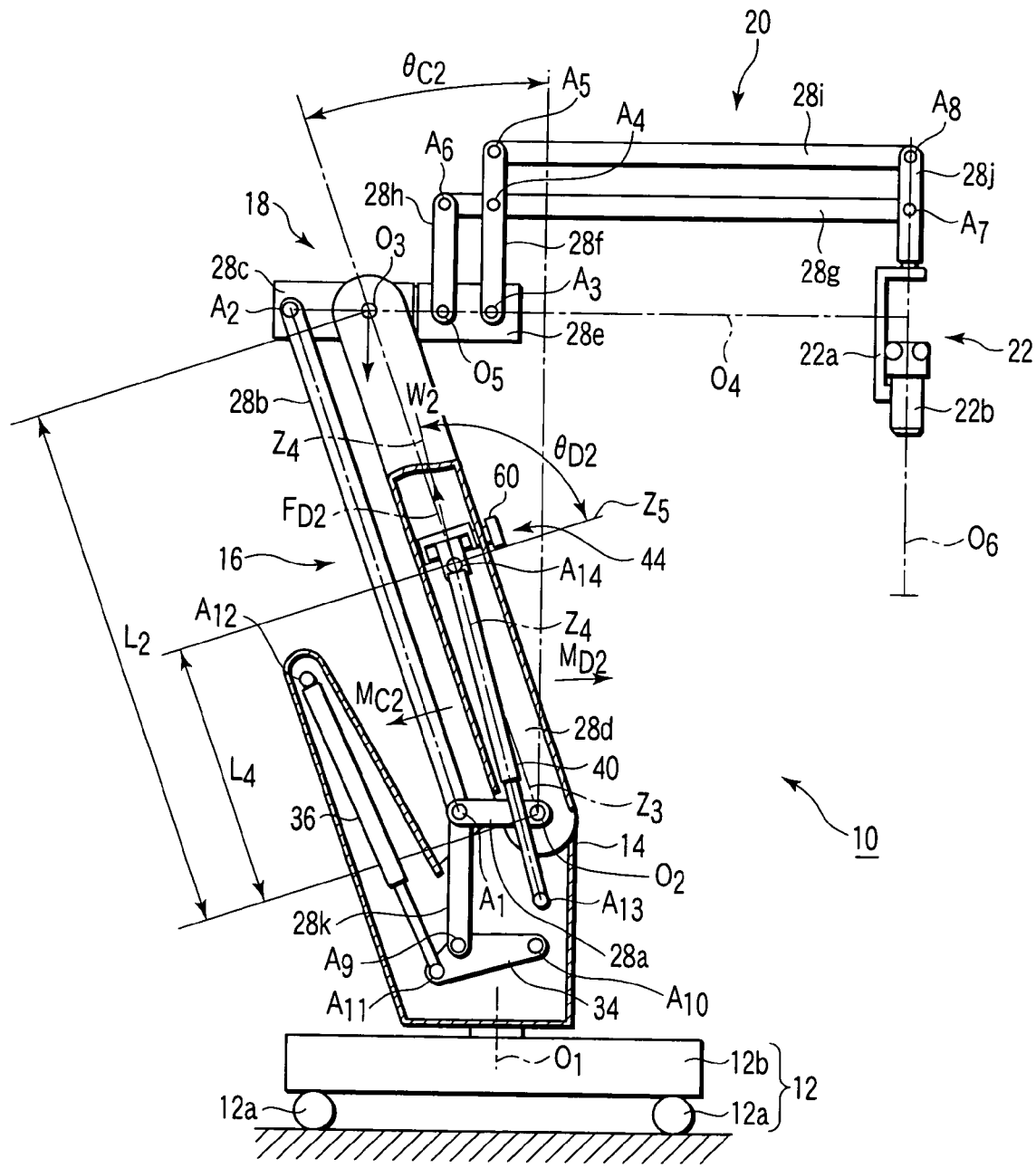
F I G. 3A

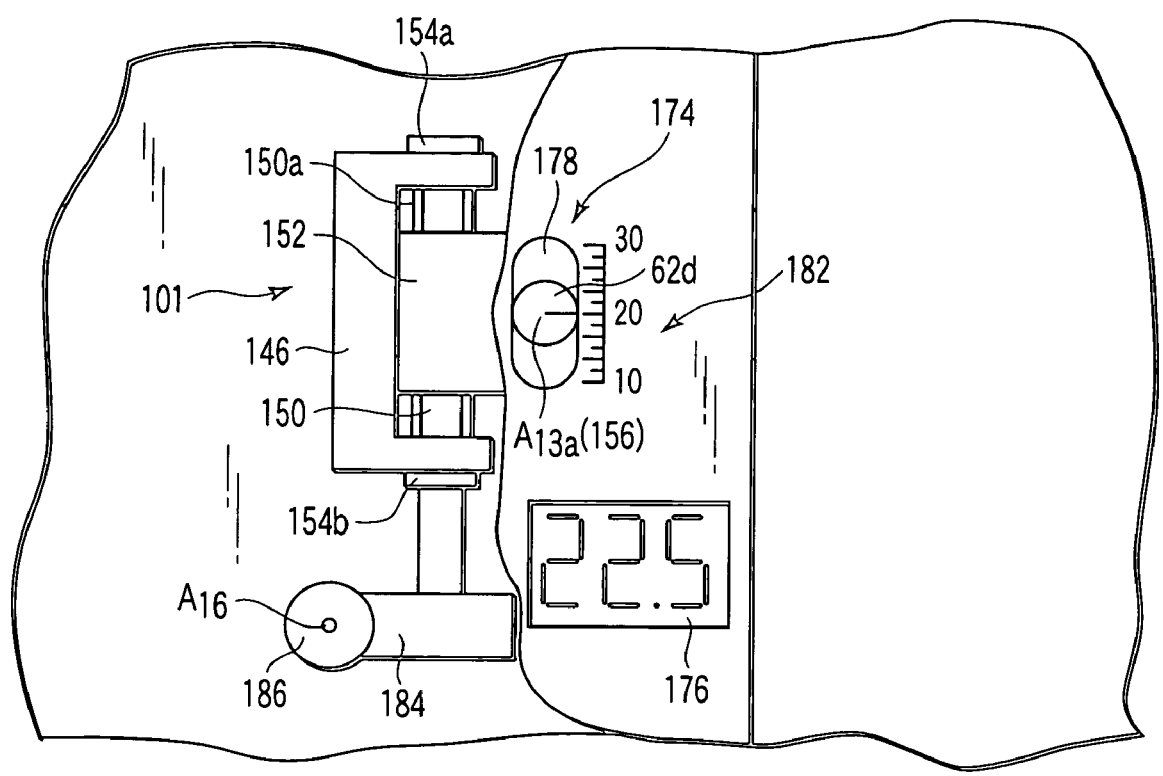
F I G. 8B

OPERATING MICROSCOPE HAVING AN ARM FRAME

CROSS-REFERENCE TO RELATED APPLICATIONS

This is a Continuation Application of PCT Application No. PCT/JP2005/000602, filed Jan. 19, 2005, which was published under PCT Article 21(2) in Japanese.

This application is based upon and claims the benefit of priority from prior Japanese Patent Application No. 2004-059811, filed Mar. 3, 2004, the entire contents of which are incorporated herein by reference.

BACKGROUND OF THE INVENTION

1. Field of the Invention

This invention relates to an operating microscope used in, for example, surgical operations.

2. Description of the Related Art

An operating microscope is disclosed in, for example, Jpn. Pat. Appln. KOKAI Publication No. 7-16239. This operating microscope has an arm frame of a counterweight (counterbalance) type in which a lens barrel portion supported on an arm is supported for three-dimensional movement and a counterweight is used for total balancing.

Disclosed in Jpn. Pat. Appln. KOKAI Publication No. 57-86806 is an operating microscope having an arm frame of a spring-balance type in which a spring is used for total balancing. This arm frame can enable the overall weight or mass of the operating microscope to be less than the counterbalance-type arm frame, that is, it can make the operating microscope more compact. Thus, this operating microscope has an advantage of improved transportability.

The operating microscope having the spring-balanced arm frame thus disclosed in Jpn. Pat. Appln. KOKAI Publication No. 57-86806 includes a horizontal motion arm, which makes a lens barrel portion horizontally move around two vertical axes, and a vertical motion arm, which makes the lens barrel portion vertically move around one horizontal axis. This arm frame has a structure such that an angular moment generated around the one horizontal axis by the weight of the lens barrel portion or the weight of the vertical motion arm is canceled for balancing by an elastic member (coil spring, gas spring, etc.).

An operating microscope is disclosed in European Pat. Appln. Publication No. 1251380. This operating microscope is furnished with a leveling function having a solid structure such that a rotary swing bearing is attached to the arm frame and two vertical axes can be adjusted for leveling in the vertical direction without regard to inclination of a floor surface.

BRIEF SUMMARY OF THE INVENTION

According to an aspect of the present invention, an operating microscope includes a base, a post, a horizontal motion arm, a vertical motion arm, a lens barrel portion, an elastic member, a fulcrum, and a fulcrum moving mechanism. The base is set on a floor surface. The post is held for rotation around a vertical rotation axis with respect to the base. The horizontal motion arm is held for rotation around a first horizontal rotation axis with respect to the post. The vertical motion arm is held for rotation around a second horizontal rotation axis with respect to the horizontal motion arm. The lens barrel portion is supported by the vertical motion arm. The elastic member is provided between the post and the horizontal motion arm and cancels an angular moment around the horizontal motion arm. The fulcrum is provided on the horizontal motion arm and receives a force from the elastic member. The fulcrum moving mechanism is configured to shift the position of the fulcrum in a direction substantially perpendicular to a longitudinal direction of the horizontal motion arm.

BRIEF DESCRIPTION OF THE SEVERAL VIEWS OF THE DRAWING

FIG. 2A is a schematic view, partially in section, showing the operating microscope according to the first embodiment and illustrating a state obtained when a vertical motion arm in a horizontal state is rocked upward;

FIG. 3A is a schematic view, partially in section, showing the operating microscope according to the first embodiment and illustrating a state obtained when a horizontal motion arm in a vertical state is rocked leftward;

FIG. 8B is a schematic view showing a spring force correcting mechanism of the operating microscope according to the fourth embodiment for adjusting the spring force of a gas spring;

DETAILED DESCRIPTION OF THE INVENTION

Best modes (hereinafter referred to as embodiments) for carrying out this invention will now be described with reference to the drawings.

A first embodiment will first be described with reference to FIGS. 1A to 5B. Here a configuration of an operating microscope 10 will be described mainly with reference to FIGS. 1A and 1B.

Figure 1A:
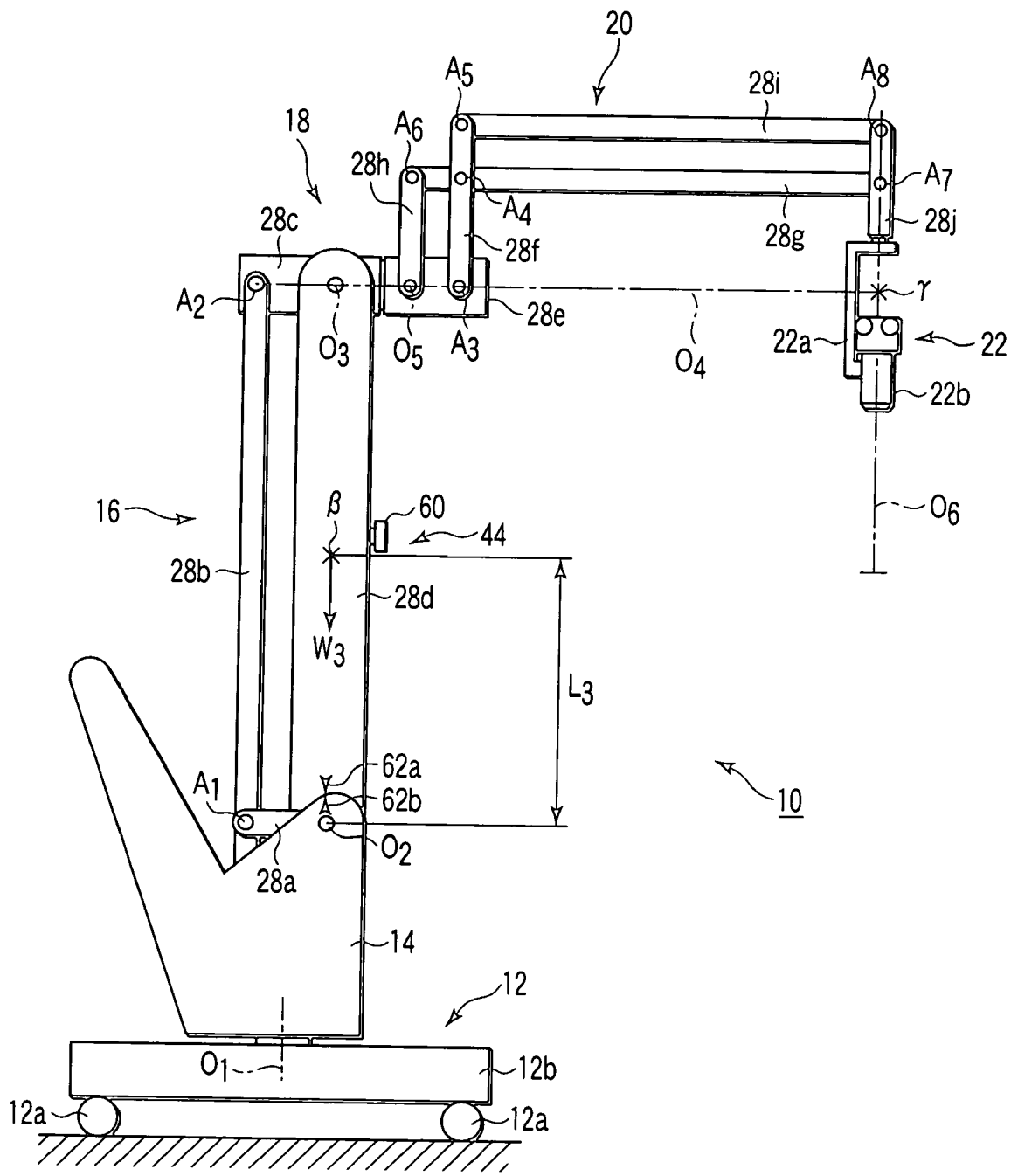
FIG. 1A is a schematic front view showing a structure of an operating microscope according to a first embodiment.

As shown in FIG. 1A, the operating microscope 10 includes a base 12, post 14, first parallelogrammic link mechanism (horizontal motion arm) 16, joint 18, second parallelogrammic link mechanism (vertical motion arm) 20, and lens barrel portion 22.

The base 12 is provided with a plurality of casters 12a, which are placed on the surface of a floor and are shiftable between a state in which they are movable in an operating room and a state in which they can be fixed, and a base body 12b located on the casters 12a. The base body 12b of the base 12 is provided with a first rotation axis $O_1$ that extends in the vertical direction. The lower end portion of the post 14 is located on the first rotation axis $O_1$ so as to be rotatable around the first rotation axis $O_1$.

Located in the upper end portion of the post 14 is a second rotation axis $O_2$ that extends in the horizontal direction at right angles to the first rotation axis $O_1$. The first parallelogrammic link mechanism 16 is located on the second rotation axis $O_2$. The first parallelogrammic link mechanism 16 is provided with first to fourth arms 28a, 28b, 28c and 28d that extend like a rod each.

The first and third arms 28a and 28c are arranged parallel to each other. The second and fourth arms 28b and 28d are arranged parallel to each other. The first and second arms 28a and 28b are connected to each other by a rotating shaft $A_1$, while the second and third arms 28b and 28c are connected to each other by a rotating shaft $A_2$. The third and fourth arms 28c and 28d are connected to each other by a third rotation axis $O_3$. The fourth and first arms 28d and 28a are connected to each other by the second rotation axis $O_2$. Further, the fourth arm 28d is connected at its lower end portion to the post 14 by the second rotation axis $O_2$.

Thus, the first to fourth arms 28a, 28b, 28c and 28d, the rotating shafts $A_1$ and $A_2$, and the second and third rotation axes $O_2$ and $O_3$ form the first parallelogrammic link mechanism 16.

The second rotation axis $O_2$ is a first horizontal rotation axis as a rocking center of the first parallelogrammic link mechanism 16 (fourth arm 28d). The third rotation axis $O_3$ is a second horizontal rotation axis as a rocking center of the second parallelogrammic link mechanism 20 (fifth, seventh, and ninth arms 28e, 28g and 28i mentioned later).

The joint 18 for connecting the first and second parallelogrammic link mechanisms 16 and 20 is located between the first and second parallelogrammic link mechanisms 16 and 20. The joint 18 is provided with a fourth rotation axis $O_4$. Specifically, the fourth rotation axis $O_4$ is located at the right-hand end portion of the third arm 28c so as to extend at right angles to the third rotation axis $O_3$. The second parallelogrammic link mechanism 20 is located on the fourth rotation axis $O_4$ so as to be rockable around the fourth rotation axis $O_4$.

The second parallelogrammic link mechanism 20 includes fifth to tenth arms 28e, 28f, 28g, 28h, 28i and 28j. The fifth, seventh, and ninth arms 28e, 28g and 28i are located parallel to one another. The sixth, eighth, and tenth arms 28f, 28h and 28j are located parallel to one another.

The fifth and sixth arms 28e and 28f are connected to each other by a rotating shaft $A_3$, while the sixth and seventh arms 28f and 28g are connected to each other by a rotating shaft $A_4$. The seventh and eighth arms 28g and 28h are connected to each other by a rotating shaft $A_6$. The fifth and eighth arms 28e and 28h are connected to each other by a fifth rotation axis $O_5$. The sixth and ninth arms 28f and 28i are connected to each other by a rotating shaft $A_5$, while the ninth and tenth arms 28i and 28j are connected to each other by a rotating shaft $A_8$. The tenth and seventh arms 28j and 28g are connected to each other by a rotating shaft $A_7$.

Thus, the fifth to tenth arms 28e, 28f, 28g, 28h, 28i and 28j, the fifth rotation axis $A_{14}$, and the rotating shafts $A_3$, $A_4$, $A_5$, $A_6$, $A_7$ and $A_8$ form the second parallelogrammic link mechanism 20.

A sixth rotation axis $O_6$ is located in the lower end portion of the tenth arm 28j so as to extend along the longitudinal axis of the tenth arm 28j. The lens barrel portion 22 is located on the sixth rotation axis $O_6$ so as to be rotatable around the sixth rotation axis $O_6$. The respective weights of the tenth arm 28j and the lens barrel portion 22 are distributed so that a synthetic center of gravity position (mass point) γ of the tenth arm 28j and the lens barrel portion 22 is substantially coincident with a point of intersection between the fourth and sixth rotation axes $O_4$ and $O_6$.

The lens barrel portion 22 is provided with a support arm 22a and a lens barrel 22b. The support arm 22a has a substantially U-shaped configuration, having one end portion (upper end portion) supported on the lower end portion of the tenth arm 28*j* and the other end portion (lower end portion) supporting the lens barrel 22*b*. The lens barrel 22*b* can serve for observation in a direction along the sixth rotation axis $O_6$.

Figure 1B:
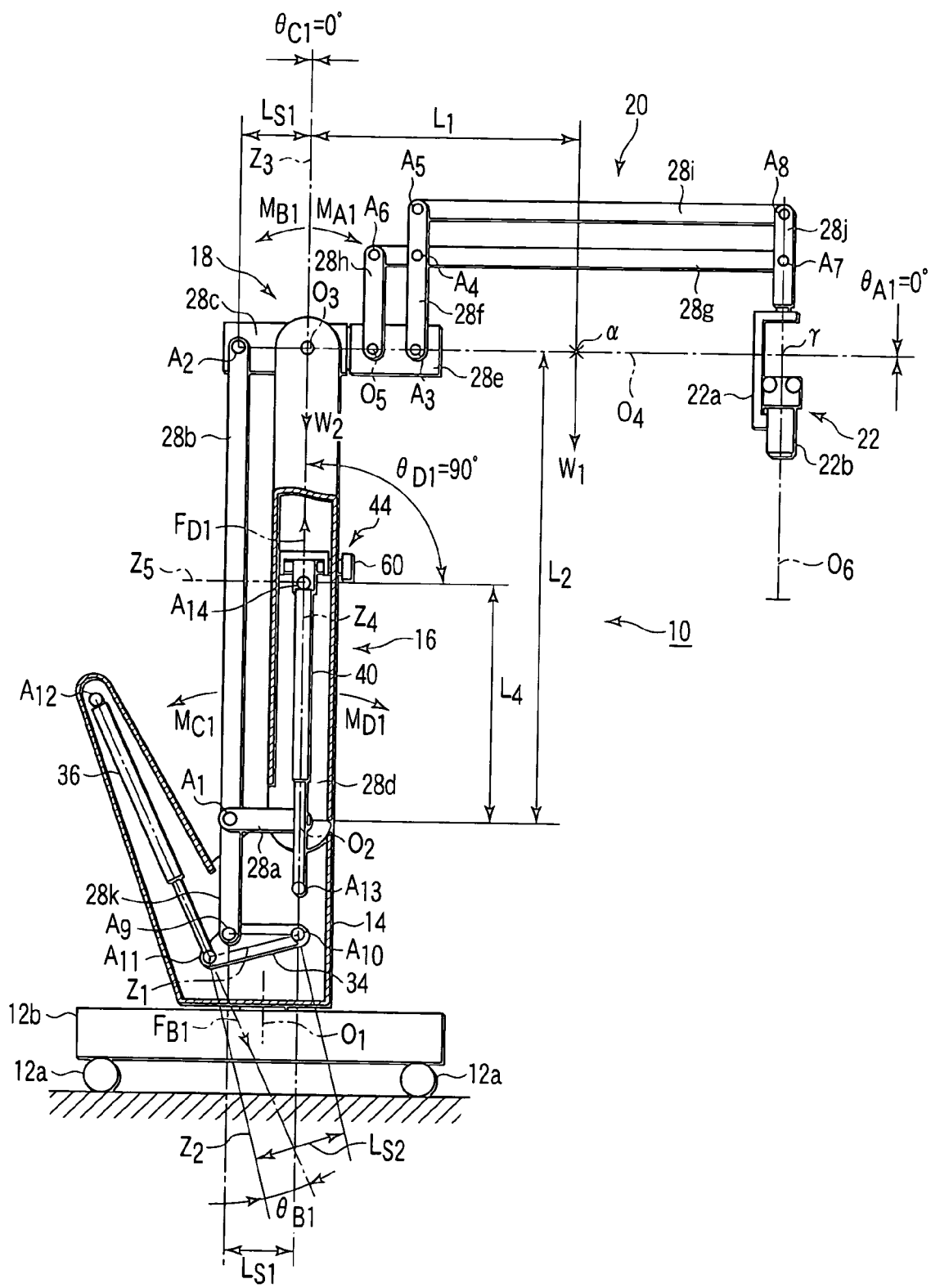
FIG. 1B is a schematic front view, partially in section, showing the operating microscope according to the first embodiment.

As shown in FIG. 1B, an eleventh arm 28*k* is contained in the post 14. The rotating shaft $A_1$ is located in the upper end portion of the eleventh arm 28*k*, and a rotating shaft $A_9$ in the lower end portion. Thus, the upper end portion of the eleventh arm 28*k* is connected to the lower end portion of the second arm 28*b* and the left-hand end portion of the first arm 28*a* by rotating shaft $A_1$.

The rotating shaft $A_9$ is located on one vertex of a triangular link 34. The triangular link 34 has three vertexes, on which rotating shafts $A_9$, $A_{10}$ and $A_{11}$ are located, individually. Under a rotating shaft $A_{13}$, which will be mentioned later, the rotating shaft $A_{10}$ is supported by the post 14. Thus, the post 14 and the triangular link 34 are connected to each other by the rotating shaft $A_{10}$. The rotating shaft $A_{11}$ is connected to one end portion (lower end portion) of a first gas spring 36.

Here the first gas spring 36 is an elastic member that balances the second parallelogrammic link mechanism 20. A rotating shaft $A_{12}$ that extends parallel to the second rotation axis $O_2$ is located on the other end portion (upper end portion) of the first gas spring 36. This rotating shaft $A_{12}$ is connected to the post 14. Thus, the post 14 and the first gas spring 36 are connected to each other by the rotating shaft $A_{12}$.

A rotating shaft $A_{13}$ that extends parallel to the second rotation axis $O_2$ is provided in the post 14. This rotating shaft $A_{13}$ is located on the same axis as the second rotation axis $O_2$. The lower end portion of a second gas spring 40, which serves as an elastic member for balancing the first parallelogrammic link mechanism 16, is rockably supported on this rotating shaft $A_{13}$. Thus, the lower end portion of the second gas spring 40 is supported on the post 14 so as to be rockable around the rotating shaft $A_{13}$ as a fulcrum (second fulcrum).

Located in the fourth arm 28*d* is a floor tilt correcting mechanism 44 that supports the upper end portion of the second gas spring 40 for rocking motion around a rotating shaft $A_{14}$. The rotating shaft $A_{14}$ is a point of application (fulcrum (first fulcrum)) of the second gas spring 40 on the fourth arm 28*d*. In an initial state, the rotating shaft $A_{14}$ is located on an axis $Z_3$ (mentioned later) that connects the second and third rotation axes $O_2$ and $O_3$.

Figure 1C:
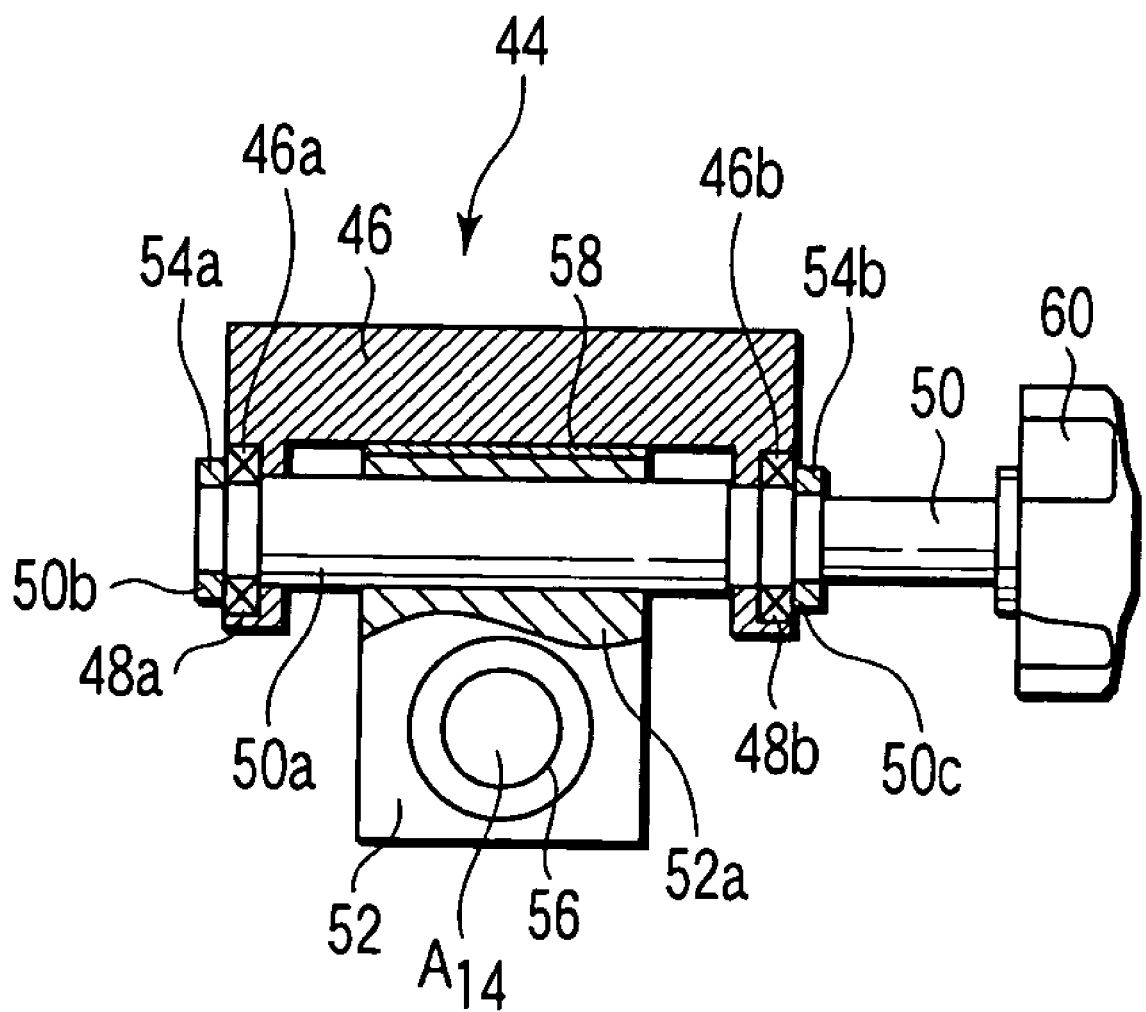
FIG. 1C is a schematic partial sectional view extractively showing a floor tilt correcting mechanism of the operating microscope shown in FIG. 1B in the operating microscope according to the first embodiment.

As shown in FIG. 1C, the floor tilt correcting mechanism 44 includes a seat 46 fixed to the fourth arm 28*d*, a pair of bearings 48*a* and 48*b*, a shaft member 50, and a slider 52.

The seat 46 is provided with a fixed portion fixed to the fourth arm 28*d* and extending portions that downwardly extend parallel to each other from the opposite end portions of the fixed portion. Seat holes 46*a* and 46*b* are formed individually in the extending portions that extend downward from the fixed portion of the seat 46. Bearings 48*a* and 48*b* are arranged in the seat holes 46*a* and 46*b*, respectively.

The shaft member 50 that has a right-handed male thread portion 50*a* on its outer peripheral surface is located in the bearings 48*a* and 48*b*. The slider 52 is located on the shaft member 50 so as to be situated between the extending portions of the seat 46. The slider 52, which is movable along the longitudinal axis of the shaft member 50, has a female thread portion 52*a* on its inner peripheral surface that threadedly mates with the male thread portion 50*a*. Thus, the shaft member 50 is rotatably disposed in the bearings 48*a* and 48*b* and the slider 52.

The shaft member 50 is located substantially at right angles to the second rotation axis $O_2$ and the axis $Z_3$ that connects the second and third rotation axes $O_2$ and $O_3$. The outer peripheral surface of the shaft member 50 is formed having male thread portions 50*b* and 50*c* in positions for the location of the bearings 48*a* and 48*b*. Retaining rings 54*a* and 54*b* are screwed on the male thread portions 50*b* and 50*c*, respectively, whereby the shaft member 50 can be prevented from slipping out of the bearings 48*a* and 48*b*.

The slider 52 is provided with a shaft portion 56 (shaft $A_{14}$) that supports the upper end portion of the second gas spring 40 for rocking motion around the rotating shaft $A_{13}$ at the lower end portion. The seat 46 and the slider 52 are arranged so that their respective flat portions face each other, and a flat resin plate 58 is fixed to the flat portion of the slider 52. If the shaft member 50 rotates, therefore, the seat 46 and the slider 52 are prevented from rotating relatively to each other, and the slider 52 moves along the axis of the shaft member 50 as the shaft member 50 rotates.

A rotary knob 60 is provided on the right-hand end portion of the shaft member 50. If the rotary knob 60 is rotated clockwise (in the right-handed direction), for example, the slider 52 moves to the right in FIG. 1C. If the rotary knob 60 is rotated counterclockwise, the slider 52 moves to the left in FIG. 1C. Thus, the floor tilt correcting mechanism 44 constitutes a fulcrum moving mechanism that supports the shaft $A_{14}$ for movement in a direction substantially perpendicular to the longitudinal axis (axis $Z_3$ that connects the second and third rotation axes $O_2$ and $O_3$) of the fourth arm 28*d* and the shaft $A_{14}$.

As shown in FIG. 1A, indexes 62*a* and 62*b* are printed on the fourth arm 28*d* and the post 14, respectively. These indexes 62*a* and 62*b* are aligned with each other when the fourth arm 28*d* is located upright with respect to the floor. Thus, the indexes 62*a* and 62*b* serve as substantial guide marks that indicate that the fourth arm 28*d* is substantially upright.

The following is a description of a balancing structure in which the second parallelogrammic link mechanism 20 is balanced by the first gas spring 36.

As shown in FIG. 1B, an angular moment $M_{A1}$ is generated around the third rotation axis $O_3$ by the respective weights of the lens barrel portion 22, the second parallelogrammic link mechanism 20 that supports the same, etc. This angular moment $M_{A1}$ is given by $$M_{A1} = W_1 \cdot L_1 \cdot \cos \theta_{A1}$$

where $W_1$ is the gross weight of the lens barrel portion 22, the second parallelogrammic link mechanism 20, etc., symbol α designates their total center of gravity position (mass point), $L_1$ is a distance from the third rotation axis $O_3$ to the center of gravity position α, and $\theta_{A1}$ is an angle between the horizontal axis and the fourth rotation axis $O_4$.

This is a moment that is generated in the clockwise direction of FIG. 1B around the third rotation axis $O_3$. In the state shown in FIG. 1B, cos 0°=1 is obtained when the fourth rotation axis $O_4$ is horizontal ($\theta_{A1}$=0°), so that the angular moment $M_{A1}$ has its maximum ($M_{A1} = W_1 \cdot L_1$).

Compared with the aforesaid angular moment $M_{A1}$, on the other hand, an angular moment $M_{B1}$ is generated around the third rotation axis $O_3$ by the spring force of the first gas spring 36. The spring force generated by the first gas spring 36 in the state shown in FIG. 1B is $F_{B1}$. Any of distances from the third rotation axis $O_3$ to the shaft $A_2$, from the second rotation axis $O_2$ to the shaft $A_1$, and from the shaft $A_{10}$ to the shaft $A_9$ is $L_{S1}$. A distance from the shaft $A_{10}$ to the shaft $A_{11}$ is $L_{S2}$. An angle between the direction of the spring force $F_{B1}$ of the first gas spring 36 and an axis $Z_2$ perpendicular to an axis $Z_1$ that connects the shafts $A_{10}$ and $A_{11}$ is $\theta_{B1}$. Since a moment generated around the shaft $A_{10}$ is set to be equivalent to the angular moment $M_{B1}$ that is generated around the third rotation axis $O_3$, this angular moment $M_{B1}$ is given by $$M_{B1}=F_{B1}\cdot(L_{S2}/L_{S1})\cdot\cos\theta_{B1}.$$

This is a moment that is generated in the counterclockwise direction of FIG. 1B around the third rotation axis $O_3$.

When the lens barrel portion 22 is moved to a position above the state shown in FIG. 1B, as shown in FIG. 2A, an angular moment $M_{A2}$ is generated around the third rotation axis $O_3$ by the respective weights of the lens barrel portion 22, the second parallelogrammic link mechanism 20 that supports the same, etc. If the angle of the fourth rotation axis $O_4$ to the horizontal axis is $\theta_{A2}$, this angular moment $M_{A2}$ is given by $$M_{A2}=W_1\cdot L_1\cdot\cos\theta_{A2}.$$

This is a moment that is generated in the clockwise direction of FIG. 2A around the third rotation axis $O_3$.

Compared with the aforesaid angular moment $M_{A2}$, on the other hand, an angular moment $M_{B2}$ is generated around the third rotation axis $O_3$ by the spring force of the first gas spring 36 in the state shown in FIG. 2A. If the spring force generated by the first gas spring 36 is $F_{B2}$ and if an angle between the direction of the spring force $F_{B2}$ and the axis $Z_2$ is $\theta_{B2}$ the angular moment $M_{B2}$ is given by $$M_{B2}=F_{B2}\cdot(L_{S2}/L_{S1})\cdot\cos\theta_{B2}.$$

This is a moment that is generated in the counterclockwise direction of FIG. 2A around the third rotation axis $O_3$.

Figure 2B:
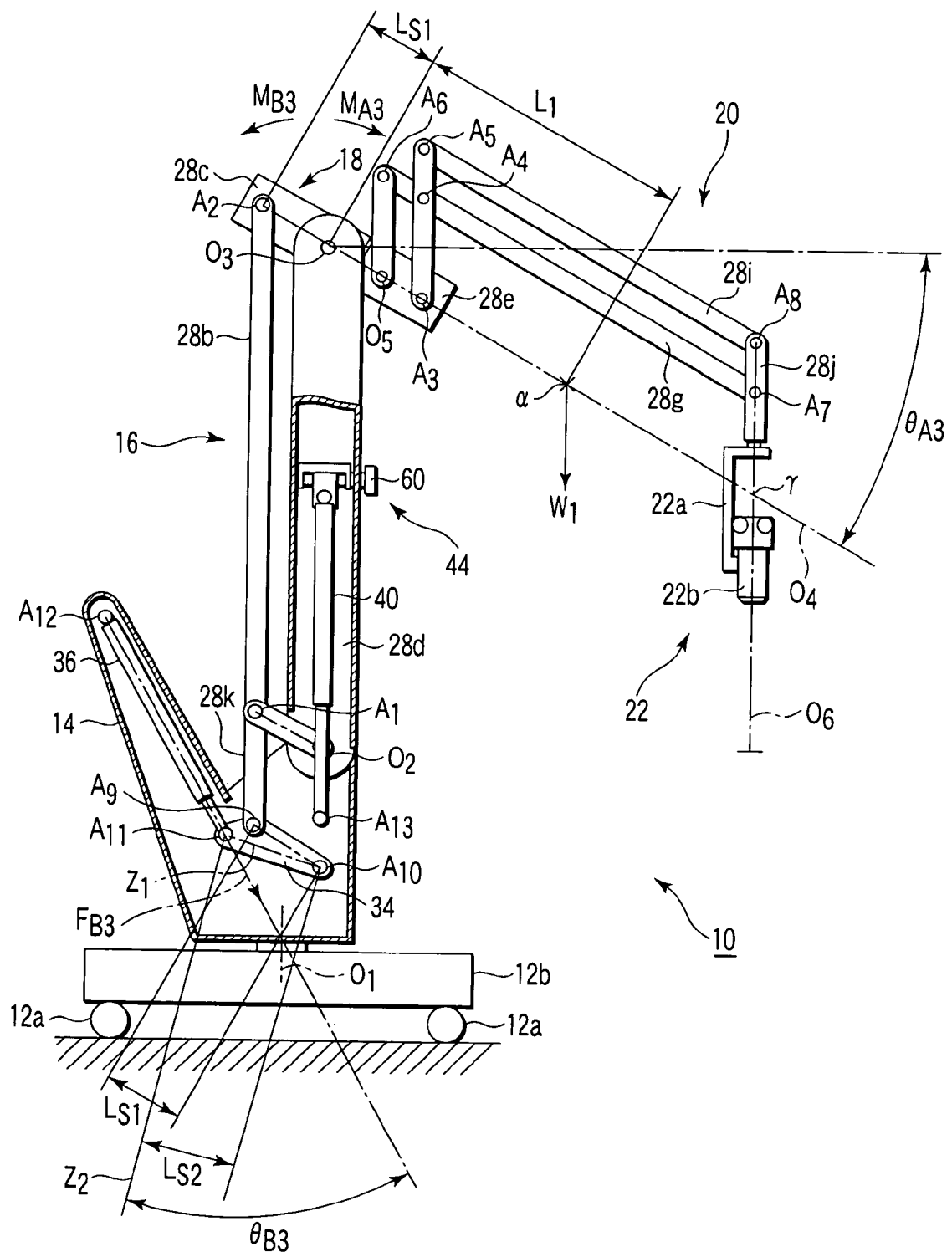
FIG. 2B is a schematic view, partially in section, showing the operating microscope according to the first embodiment and illustrating a state obtained when the vertical motion arm in the horizontal state is rocked downward.

FIG. 2B illustrates a state obtained when the lens barrel portion 22 in the state shown in FIG. 1B is moved downward and the third arm 28c is rotated counterclockwise around the third rotation axis $O_3$. In the state shown in FIG. 2B, an angular moment $M_{A3}$ is generated around the third rotation axis $O_3$ by the respective weights of the lens barrel portion 22, the second parallelogrammic link mechanism 20 that supports the same, etc. This angular moment $M_{A3}$ is given by $$M_{A3}=W_1\cdot L_1\cdot\cos\theta_{A3}$$

where $\theta_{A3}$ is an angle between the horizontal axis and the fourth rotation axis $O_4$.

This is a moment that is generated in the clockwise direction of FIG. 2B around the third rotation axis $O_3$.

In the state shown in FIG. 2B, on the other hand, an angular moment $M_{B3}$ is generated around the third rotation axis $O_3$ by the spring force of the first gas spring 36. If the spring force generated by the first gas spring 36 is $F_{B3}$ and if an angle between the direction of the spring force $F_{B3}$ generated by the first gas spring 36 and the axis $Z_2$ is $\theta_{B3}$, the angular moment $M_{B3}$ is given by $$M_{B3}=F_{B3}\cdot(L_{S2}/L_{S1})\cdot\cos\theta_{B3}.$$

This is a moment that is generated in the counterclockwise direction of FIG. 2B around the third rotation axis $O_3$.

The shafts $A_9$, $A_{11}$ and $A_{12}$ are located relatively to the shaft $A_{10}$ and the spring force of the first gas spring 36 is selected so that the angular moments $M_{A1}$ and $M_{B1}$ are substantially equal to each other in the state (initial state) shown in FIG. 1B. Likewise, the shafts $A_9$, $A_{11}$ and $A_{12}$ are located relatively to the shaft $A_{10}$ and the spring force of the first gas spring 36 is selected so that the angular moments $M_{A2}$ and $M_{B2}$ are substantially equal to each other in the state shown in FIG. 2A and that the angular moments $M_{A3}$ and $M_{B3}$ are so in the state shown in FIG. 2B.

The following is a description of a balancing structure in which the first parallelogrammic link mechanism 16 is balanced by the second gas spring 40.

In the state shown in FIG. 1B, an angular moment $M_{C1}$ is generated around the second rotation axis $O_2$ by the respective weights of the lens barrel portion 22, the first and second parallelogrammic link mechanism 16 and 20 that support the same, etc. The weight load of the lens barrel portion 22, the second parallelogrammic link mechanism 20, etc., which acts on the third rotation axis $O_3$, is $W_2$. The weight of the fourth arm 28d is $W_3$, and its center of gravity position (mass point) β is located on the axis $Z_3$ that connects the second rotation axis $O_2$ and the third rotation axis $O_3$. A distance from the second rotation axis $O_2$ to the third rotation axis $O_3$ is supposed to be $L_2$. A distance from the second rotation axis $O_2$ to the center of gravity position β of the weight $W_3$ is supposed to be $L_3$. An angle between a vertical axis and the axis $Z_3$ that connects the second rotation axis $O_2$ and the third rotation axis $O_3$ is supposed to be $\theta_{C1}$. Thereupon, the angular moment $M_{C1}$ is given by $$M_{C1}=(W_2\cdot L_2+W_3\cdot L_3)\sin\theta_{C1}.$$

When the fourth arm 28d (axis $Z_3$) is inclined counterclockwise (or to the left) around the second rotation axis $O_2$ with respect to the vertical axis, the angular moment $M_{C1}$ is generated in the counterclockwise direction around the second rotation axis $O_2$. When the fourth arm 28d is inclined clockwise (or to the right) around the second rotation axis $O_2$ with respect to the vertical axis, on the other hand, the angular moment $M_{C1}$ is generated in the clockwise direction around the second rotation axis $O_2$. In the state shown in FIG. 1B, the axis $Z_3$ is vertical ($\theta_{C1}=0°$) and $\sin\theta_{C1}=0$ is obtained, so that the angular moment $M_{C1}$ is 0 (zero).

On the other hand, an angular moment $M_{D1}$ is generated around the second rotation axis $O_2$ by the spring force of the second gas spring 40.

In the state shown in FIG. 1B, the spring force generated by the second gas spring 40 is $F_{D1}$. A distance from the second rotation axis $O_2$ to the rotating shaft $A_{14}$ is $L_4$. An angle between the direction of the spring force $F_{D1}$ of the second gas spring 40 and a axis $Z_5$ perpendicular to an axis $Z_4$ that connects the second rotation axis $O_2$ and the shaft $A_{14}$ is supposed to be $\theta_{D1}$. Thereupon, the angular moment $M_{D1}$ is given by $$M_{D1}=F_{D1}\cdot L_4\cdot\cos\theta_{D1}.$$

When the direction of the spring force $F_{D1}$ of the second gas spring 40 is inclined clockwise around the rotating shaft $A_{14}$ with respect to the axis $Z_4$, the angular moment $M_{D1}$ is generated in the clockwise direction around the second rotation axis $O_2$. When the direction of the spring force $F_{D1}$ is inclined counterclockwise around the rotating shaft $A_{14}$, on the other hand, the angular moment $M_{D1}$ is generated in the counterclockwise direction around the second rotation axis $O_2$. Since the angle $\theta_{D1}=90°$ in FIG. 1B, $\cos\theta_{D1}=0$ is obtained, so that the angular moment $M_{D1}$ is 0 (zero).

FIG. 3A illustrates a state obtained when the lens barrel portion 22 in the state shown in FIG. 1B is moved backward (or to the side nearer to the first rotation axis $O_1$) and the fourth arm 28d is rocked counterclockwise around the second rotation axis $O_2$. In the state shown in FIG. 3A, an angular moment $M_{C2}$ is generated around the second rotation axis $O_2$ by the respective weights of the lens barrel portion 22, the first and second parallelogrammic link mechanisms 16 and 20 that support the same, etc. If the angle of the axis $Z_3$ to the vertical axis is $\theta_{C2}$, the angular moment $M_{C2}$ is given by $$M_{C2}=(W_2\cdot L_2+W_3\cdot L_3)\sin\theta_{C2}.$$

This is a moment that is generated in the counterclockwise direction of FIG. 3A around the second rotation axis $O_2$.

In the state shown in FIG. 3A, on the other hand, an angular moment $M_{D2}$ is generated around the second rotation axis $O_2$ by the spring force of the second gas spring 40. In the state shown in FIG. 3A, the spring force generated by the second gas spring 40 is $F_{D2}$. An angle between the direction of the spring force $F_{D2}$ of the second gas spring 40 and the axis $Z_5$ is supposed to be $\theta_{D2}$. Thereupon, the angular moment $M_{D2}$ is given by $$M_{D2}=F_{D2} \cdot L_4 \cdot \cos\theta_{D2}.$$

This is a moment that is generated in the clockwise direction of FIG. 3A around the second rotation axis $O_2$.

Figure 3B:
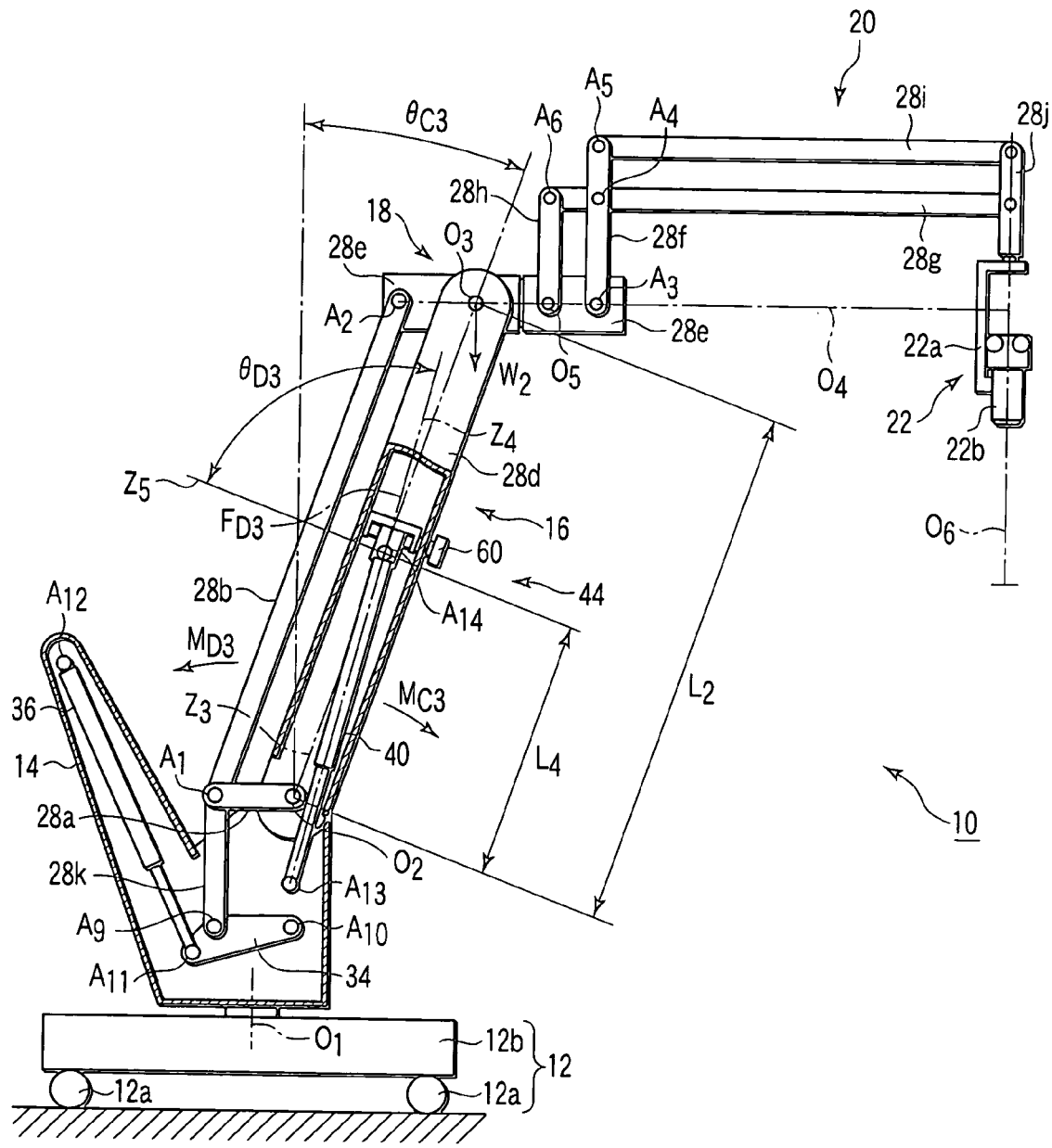
FIG. 3B is a schematic view, partially in section, showing the operating microscope according to the first embodiment and illustrating a state obtained when the horizontal motion arm in the vertical state is rocked rightward.

FIG. 3B illustrates a state obtained when the lens barrel portion 22 in the state shown in FIG. 1B is moved forward (to the side remoter from the first rotation axis $O_1$) and the fourth arm 28d is rocked clockwise around the second rotation axis $O_2$. In the state shown in FIG. 3B, an angular moment $M_{C3}$ is generated around the second rotation axis $O_2$ by the respective weights of the lens barrel portion 22, the second parallelogrammic link mechanism 20 that supports the same, etc. If the angle of the axis $Z_3$ to the vertical axis is $\theta_{C3}$, the angular moment $M_{C3}$ is given by $$M_{C3}=(W_2 \cdot L_2 + W_3 \cdot L_3)\sin\theta_{C3}.$$

This is a moment that is generated in the clockwise direction of FIG. 3B around the second rotation axis $O_2$.

In the state shown in FIG. 3B, on the other hand, an angular moment $M_{D3}$ is generated around the second rotation axis $O_2$ by the spring force of the second gas spring 40. In the state shown in FIG. 3B, the spring force generated by the second gas spring 40 is $F_{D3}$. An angle between the direction of the spring force $F_{D3}$ of the second gas spring 40 and the axis $Z_5$ is supposed to be $\theta_{D3}$. Thereupon, the angular moment $M_{D3}$ is given by $$M_{D3}=F_{D3} \cdot L_4 \cdot \cos\theta_{D3}.$$

This is a moment that is generated in the counterclockwise direction of FIG. 3B around the second rotation axis $O_2$.

The rotating shafts $A_{13}$ and $A_{14}$ are located relatively to the second rotation axis $O_2$ and the spring force of the second gas spring 40 is selected so that the angular moments $M_{C1}$ and $M_{D1}$ are substantially equal to each other in the state (initial state) shown in FIG. 1B. Likewise, the rotating shafts $A_{13}$ and $A_{14}$ are located relatively to the second rotation axis $O_2$ and the spring force of the second gas spring 40 is selected so that the angular moments $M_{C2}$ and $M_{D2}$ are substantially equal to each other in the state shown in FIG. 3A and that the angular moments $M_{C3}$ and $M_{D3}$ are so in the state shown in FIG. 3B.

The following is a description of a balancing structure in which the first parallelogrammic link mechanism 16 is balanced by the second gas spring 40 when the floor is inclined.

Figure 4A:
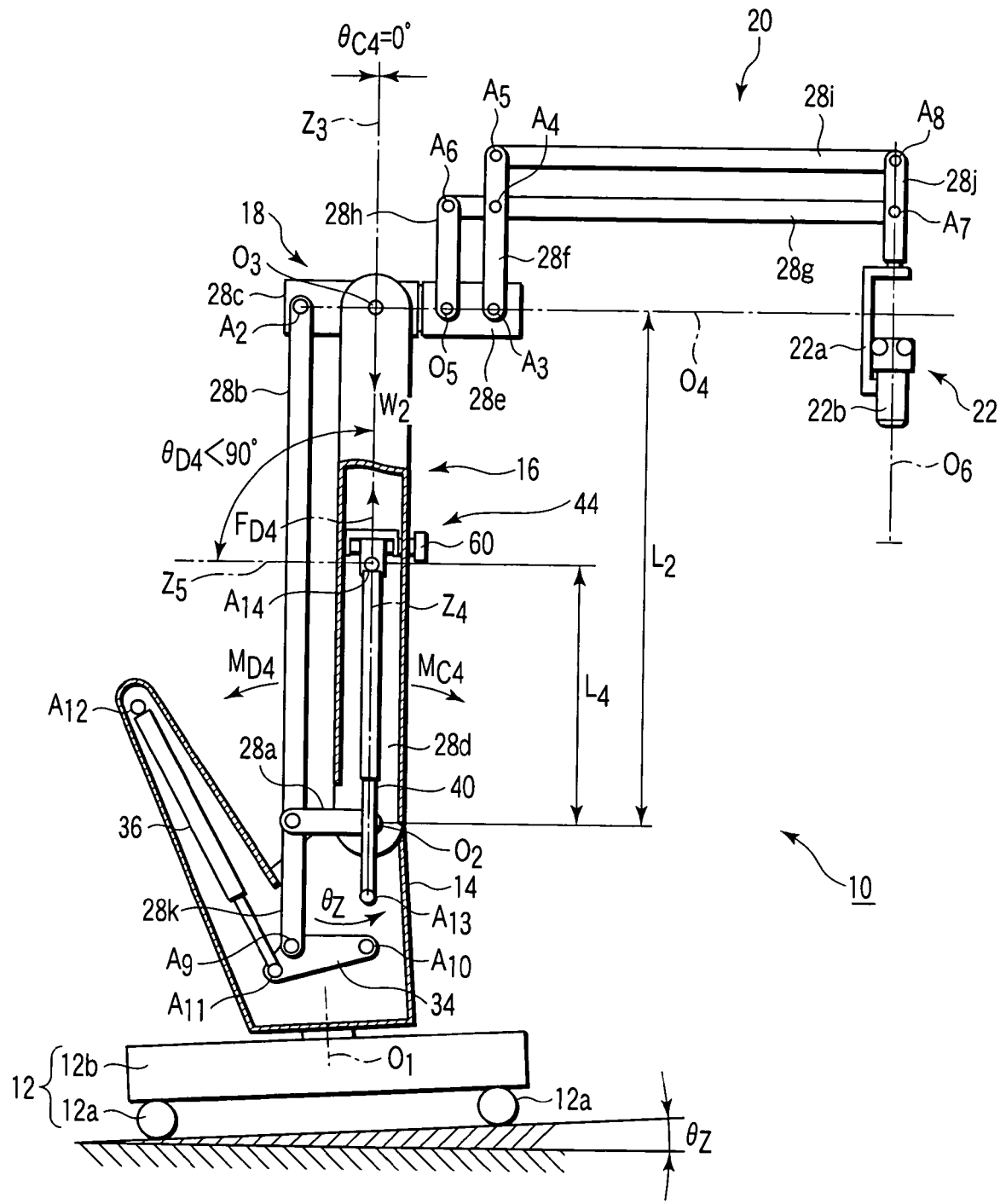
FIG. 4A is a front view, partially in section, showing the operating microscope according to the first embodiment and illustrating a state in which the operating microscope is located on an inclined floor with the horizontal motion arm in a vertical posture.

FIG. 4A, which is similar to FIG. 1A, illustrates a state in which the operating microscope 10 is located on a floor surface that is inclined at a tilt angle $\theta_Z$ to a horizontal state with the fourth arm 28d (axis $Z_3$) kept in a vertical posture. The operating microscope 10 is located on a slope, which is raised on the right-hand side in FIG. 4A so that its left-hand side is lower than the right-hand side, in a manner such that the first rotation axis $O_1$ of the operating microscope 10 is inclined at the angle $\theta_Z$.

Since the base 12 and the post 14 are thus tilted as they are located in place, the position of the shaft $A_{13}$ that is fixed inside the post 14 shifts to a position reached when the system set on a level floor is rocked counterclockwise for the tilt angle $\theta_Z$ around the second rotation axis $O_2$.

In the state shown in FIG. 4A, an angular moment $M_{C4}$ is generated around the second rotation axis $O_2$ by the respective weights of the lens barrel portion 22, the second parallelogrammic link mechanism 20 that supports the same, etc. If the angle of the axis $Z_3$ to the vertical axis is $\theta_{C4}$, the angular moment $M_{C4}$ is given by $$M_{C4}=(W_2 \cdot L_2 + W_3 \cdot L_3)\sin\theta_{C4}.$$

Since the vertical axis and the axis $Z_3$ extend in the same direction, the angle $\theta_{C4}=0°$, so that $\sin\theta_{C4}=0$ is obtained, and therefore, the angular moment is $M_{C4}=0$. This is not different from the aforesaid angular moment $M_{C1}$ shown in FIG. 1B.

In the state shown in FIG. 4A, on the other hand, an angular moment $M_{D4}$ is generated around the second rotation axis $O_2$ by the spring force of the second gas spring 40. In the state shown in FIG. 4A, the spring force generated by the second gas spring 40 is $F_{D4}$. An angle between the direction of the spring force $F_{D4}$ of the second gas spring 40 and the axis $Z_5$ is supposed to be $\theta_{D4}$. Thereupon, the angular moment $M_{D4}$ is given by $$M_{D4}=F_{D4} \cdot L_4 \cdot \cos\theta_{D4}.$$

The angle $\theta_{D1}$ shown in FIG. 1B described above is $\theta_{D1}=90°$. Therefore, the angular moment $M_{D1}$ is 0. Since the position of the shaft $A_{13}$ is rocked for the tilt angle $\theta_Z$ around the second rotation axis $O_2$ so that the angle $\theta_{D4}$ is smaller than 90°, so that the angular moment $M_{D4}$ is not 0. This is a moment that is generated in the counterclockwise direction of FIG. 4A around the second rotation axis $O_2$. While the angular moment $M_{C4}$ is 0, there exists the angular moment $M_{D4}$ that is generated in the counterclockwise direction around the second rotation axis $O_2$. Thus, the fourth arm 28d tilts backward (or to the left in FIG. 4A) around the second rotation axis $O_2$.

Figure 4B:
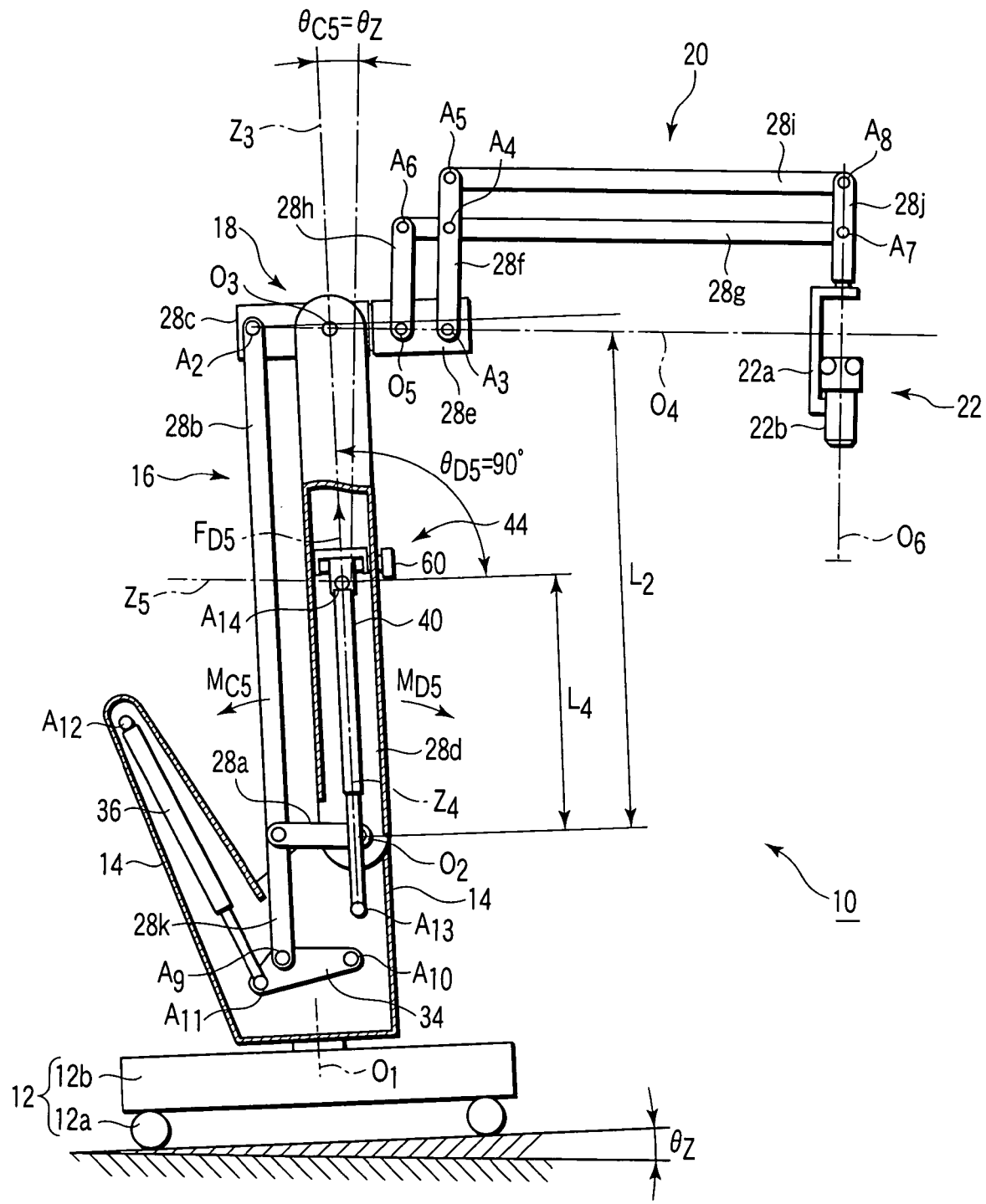
FIG. 4B is a schematic view, partially in section, showing the operating microscope according to the first embodiment and illustrating a state in which the horizontal motion arm is postured to extend substantially at right angles to the inclined floor.

FIG. 4B illustrates a state in which the operating microscope 10 in the state shown in FIG. 1B is set on a floor that is inclined at the tilt angle $\theta_Z$. Thus, the fourth arm 28d is not in a vertical posture, and its axial direction is parallel to the first rotation axis $O_1$.

In the state shown in FIG. 4B, the center of gravity position of the first parallelogrammic link mechanism 16 that includes the second and fourth arms 28b and 28d is shifted to the left without being situated on a vertical axis that passes through the second rotation axis $O_2$ as the second and fourth arms 28b and 28d tilt. Thus, in the state shown in FIG. 4B, an angular moment $M_{C5}$ is generated around the second rotation axis $O_2$ by the respective weights of the lens barrel portion 22, the second parallelogrammic link mechanism 20 that supports the same, etc. If the angle of the axis $Z_3$ to the vertical axis is $\theta_{C5}$, the angular moment $M_{C5}$ is given by $$M_{C5}=(W_2 \cdot L_2 + W_3 \cdot L_3)\sin\theta_{C5}.$$

Since the angle $\theta_{C5}$ is equal to $\theta_Z$, $M_{C5}$ is given by $$M_{C5}=(W_2 \cdot L_2 + W_3 \cdot L_3)\sin\theta_Z.$$

This is a moment that is generated in the counterclockwise direction of FIG. 4B around the second rotation axis $O_2$.

In the state shown in FIG. 4B, on the other hand, an angular moment $M_{D5}$ is generated around the second rotation axis $O_2$ by the spring force of the second gas spring 40. In the state shown in FIG. 4B, the spring force generated by the second gas spring 40 is $F_{D5}$. An angle between the direction of the spring force $F_{D5}$ of the second gas spring 40 and the axis $Z_5$ is supposed to be $\theta_{D5}$. Thereupon, the angular moment $M_{D5}$ is given by $$M_{D5}=F_{D5} \cdot L_5 \cdot \cos\theta_{D5}.$$

Since the angle $\theta_{D5}$ is 90°, $\cos\theta_{D5}$ is 0, and the angular moment $M_{D5}$ is 0. While the angular moment $M_{D5}$ is 0, there exists the angular moment $M_{C5}$ that is generated in the counterclockwise direction around the second rotation axis $O_2$. Thus, the fourth arm 28d tilts backward (or to the left in FIG. 4B) around the second rotation axis $O_2$.

If the floor on which the operating microscope 10 is set has the tilt angle $\theta_Z$ with its right-hand side higher than the left-hand side, as shown in FIGS. 4A and 4B, the rotating shaft (fulcrum) $A_{13}$ under the second gas spring 40 rocks counterclockwise for the tilt angle $\theta_Z$ with respect to the second rotation axis $O_2$. Thereupon, the rotating shaft (fulcrum) $A_{14}$ (shaft portion 56) on the fourth arm 28d is rocked counterclockwise around the rotating shaft $A_{13}$ by the second gas spring 40, so that the fourth arm 28d is subjected to a heavier counterclockwise moment than when the system is set on a level floor.

If the floor is inclined reversely (so that the operating microscope 10 is located on a slope, which is lowered on the right-hand side in FIG. 4A so that its left-hand side is higher than the right-hand side, in a manner such that the first rotation axis $O_1$ of the operating microscope 10 is inclined at the angle $\theta_Z$), as compared with the states shown in FIGS. 4A and 4B, on the other hand, the rotating shaft (fulcrum) $A_{14}$ is rocked clockwise around the shaft $A_{13}$ by the second gas spring 40. Thus, the fourth arm 28d is subjected to a heavier clockwise moment.

Figure 5A:
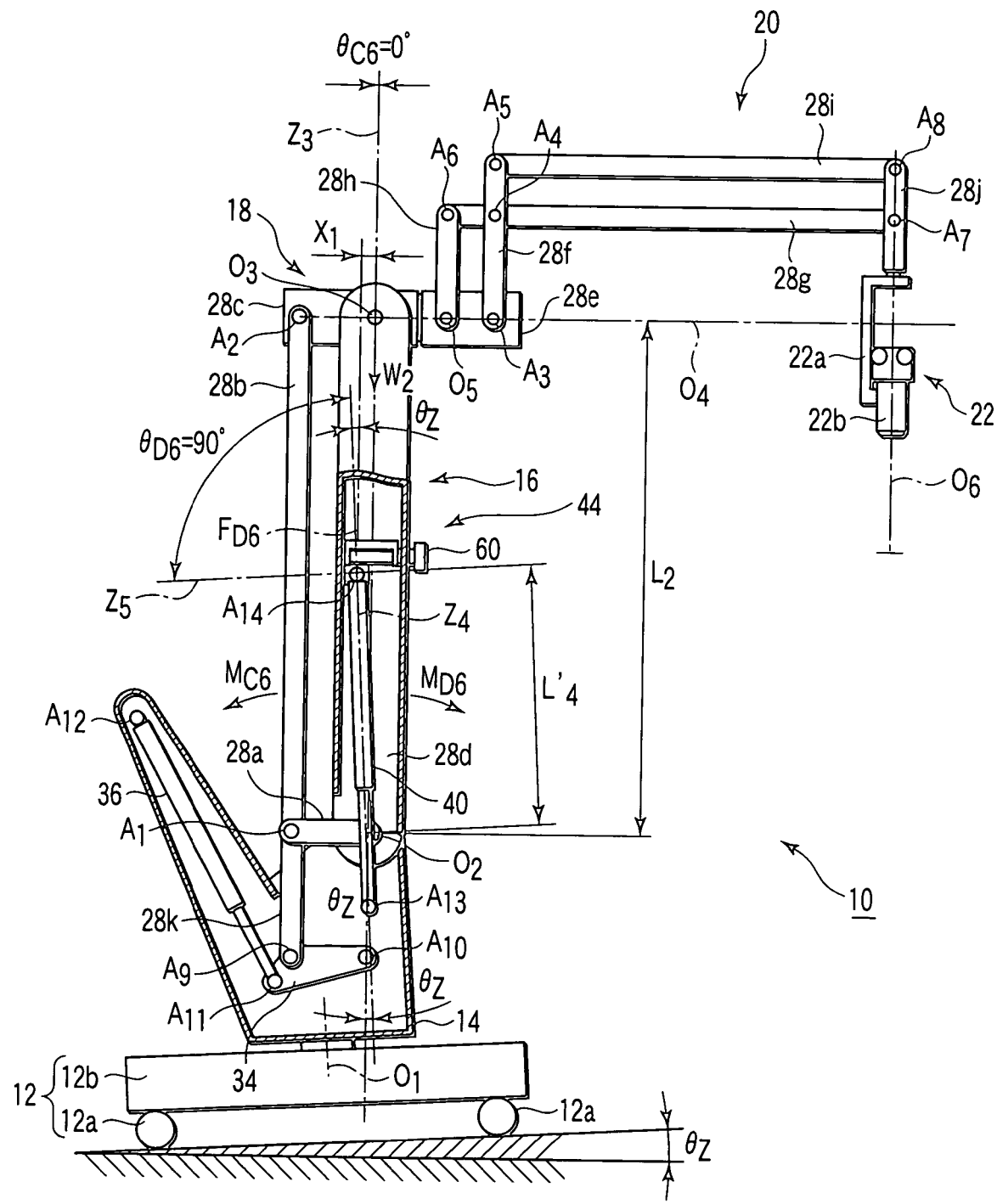
FIG. 5A is a front view, partially in section and corresponding to FIG. 4A, showing the operating microscope according to the first embodiment and illustrating a state in which the operating microscope is located on the inclined floor with the horizontal motion arm in a corrected vertical state.

FIG. 5A, which corresponds to FIG. 4A, illustrates a state in which the operating microscope 10 is located on a floor that is inclined at the tilt angle $\theta_Z$ to a horizontal plane so that its right-hand side in FIG. 5A is higher than the left-hand side. The fourth arm 28d is in a vertical posture. In this illustrated state, the rotating shaft $A_{14}$ is moved counterclockwise around the rotating shaft $A_{13}$ for a distance equivalent to the tilt angle $\theta_Z$. This state shares other conditions with the aforementioned state shown in FIG. 4A.

The aforementioned floor tilt correcting mechanism 44 is used in moving the rotating shaft $A_{14}$ counterclockwise around the rotating shaft $A_{13}$ for the tilt angle $\theta_Z$. If the rotary knob 60 of the floor tilt correcting mechanism 44 shown in FIG. 1C is rotated counterclockwise, the slider 52 and the slider 52 (shaft portion 56) that supports an end portion of the second gas spring 40 are moved to the left in FIG. 1C.

If the rotating shaft $A_{14}$ is moved from the position on the axis $Z_3$ to the left for a movement amount $X_1$, as shown in FIG. 5A, then the rotating shaft $A_{14}$ is rocked counterclockwise for the tilt angle $\theta_Z$ with respect to the second rotation axis $O_2$. In this state, the movement amount $X_1$ is smaller than the distance $L_4$ from the second rotation axis $O_2$ to the rotating shaft $A_{14}$, so that a distance $L_{4'}$ from a position corresponding to the second rotation axis $O_2$ to the rotating shaft $A_{14}$ can be approximated to $L_4$, that is, $L_{4'}=L_4$. Thus, the movement amount $X_1$ is given by $$X_1 = L_4 \cdot \sin \theta_Z.$$

If the angle of the axis $Z_3$ to the vertical axis is $\theta_{C6}$; in the state shown in FIG. 5A, an angular moment $M_{C6}$ that is generated around the second rotation axis $O_2$ by the respective weights of the lens barrel portion 22, the first and second parallelogrammic link mechanisms 16 and 20 that support the same, etc. is given by $$M_{C6} = (W_2 \cdot L_2 + W_3 \cdot L_3) \sin \theta_{C6}.$$

Since the axis $Z_3$ of the fourth arm 28d is in a vertical posture, the axis $Z_3$ is vertical ($\theta_{C1}=0°$), so that $\sin \theta_{C6}=0$ is obtained, and therefore, the angular moment is $M_{C6}=0$.

In the state shown in FIG. 5A, on the other hand, an angular moment $M_{D6}$ is generated around the second rotation axis $O_2$ by the spring force of the second gas spring 40. In the state shown in FIG. 5A, the spring force generated by the second gas spring 40 is $F_{D6}$. An angle between the direction of the spring force $F_{D6}$ of the second gas spring 40 and the axis $Z_5$ is supposed to be $\theta_{D6}$. Thereupon, the angular moment $M_{D6}$ is given by $$M_{D6} = F_{D6} \cdot L_4 \cdot \cos \theta_{D6}.$$

Since the angle $\theta_{D6}$ is 90°, $\cos \theta_{D6}$ is 0, and the angular moment $M_{D6}$ is 0. Since the angular moment $M_{C6}=M_{D6}=0$ is given in this case, the fourth arm 28d rests.

Figure 5B:
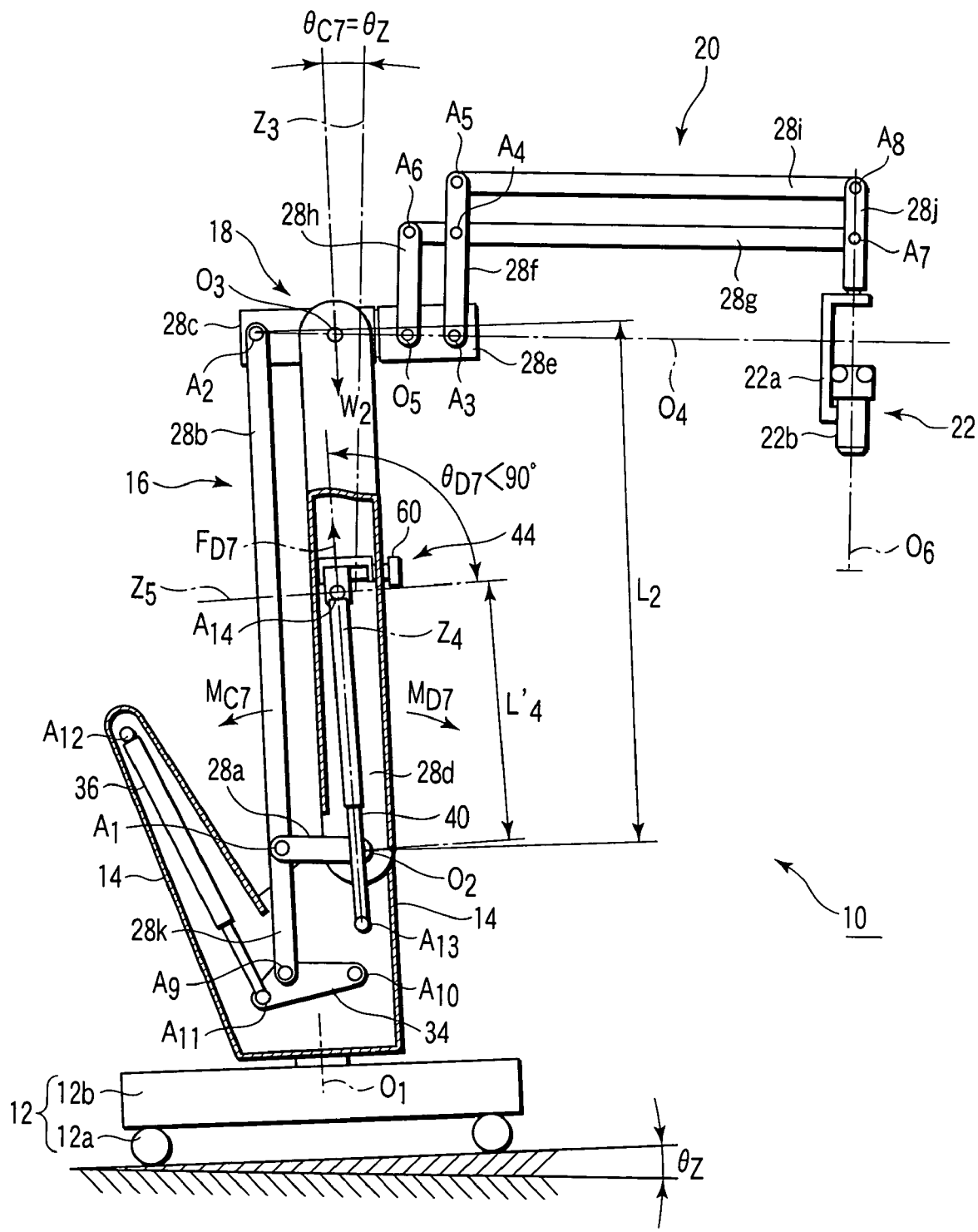
FIG. 5B is a front view, partially in section and corresponding to FIG. 4B, showing the operating microscope according to the first embodiment and illustrating a state obtained when the horizontal motion arm in the vertical state is inclined at an angle corresponding to the inclination of the floor.

FIG. 5B, which corresponds to FIG. 4B, illustrates a state in which the operating microscope 10 is located on a floor that is inclined at the tilt angle $\theta_Z$ so that its right-hand side in FIG. 5B is higher than the left-hand side. The fourth arm 28d is not in a vertical posture but in a posture such that it extends at right angles to the inclined floor. In this illustrated state, the rotating shaft $A_{14}$ is moved counterclockwise around the rotating shaft $A_{13}$ for a distance equivalent to the tilt angle $\theta_Z$. This state shares other conditions with the aforementioned state shown in FIG. 4B.

In the state shown in FIG. 5B, the center of gravity position of the first parallelogrammic link mechanism 16 that includes the second and fourth arms 28b and 28d is shifted to the left without being situated on the vertical axis that passes through the second rotation axis $O_2$ as the second and fourth arms 28b and 28d tilt. Thus, in the state shown in FIG. 5B, an angular moment $M_{C7}$ is generated around the second rotation axis $O_2$ by the respective weights of the lens barrel portion 22, the first and second parallelogrammic link mechanisms 16 and 20 that support the same, etc. If the angle of the axis $Z_3$ to the vertical axis is $\theta_{C7}$, the angular moment $M_{C7}$ is given by $$M_{C7} = (W_2 \cdot L_2 + W_3 \cdot L_3) \sin \theta_{C7}.$$

This is a moment that is generated in the counterclockwise direction of FIG. 5B around the second rotation axis $O_2$.

In the state shown in FIG. 5B, on the other hand, an angular moment $M_{D7}$ is generated around the second rotation axis $O_2$ by the spring force of the second gas spring 40. If the spring force generated by the second gas spring 40 is $F_{D7}$ and if an angle between the direction of the spring force $F_{D7}$ of the second gas spring 40 and the axis $Z_2$ is $\theta_{D7}$, in the state shown in FIG. 5B, the angular moment $M_{D7}$ is given by $$M_{D7} = F_{D7} \cdot L_4 \cdot \cos \theta_{D7}.$$

This is a moment that is generated in the clockwise direction of FIG. 5B around the second rotation axis $O_2$. Since the angular moment $M_{C7}=M_{D7}$ is given in this case, the fourth arm 28d rests.

Thus, the moment $M_C$ that is generated around the second rotation axis $O_2$ by the respective weights of the lens barrel portion 22, the first and second parallelogrammic link mechanisms 16 and 20 that support the same, etc. is settled depending on the tilt angle $\theta_Z$ to the vertical direction. If the same posture is taken on the second rotation axis $O_2$, therefore, the moment does no change, regardless of an inclination of the floor.

On the other hand, the moment $M_D$ that is generated by the spring force $F_D$ of the second gas spring 40 is determined by three elements including (1) the spring force $F_D$ of the second gas spring 40, (2) the distance $L_4$ from the center of rotation (second rotation axis $O_2$) to the fulcrum $A_{14}$, (3) the angle $\theta_D$ between the axis $Z_5$ perpendicular to the axis $Z_4$ that connects the second rotation axis $O_2$ and the shaft $A_{14}$ and the direction of the spring force $F_D$ of the second gas spring 40.

The angle $\theta_D$ of item (3) is influenced by the inclination of the floor, since the second gas spring 40 rocks relatively to fourth arm 28d around the lower fulcrum (shaft $A_{13}$) so that the angle between the direction of the spring force $F_D$ and the axis $Z_5$ perpendicular to an axis $Z_4$ that connects the center of rocking (second rotation axis $O_2$) and the upper fulcrum (shaft $A_{14}$) changes.

The floor tilt correcting mechanism 44 causes the upper fulcrum (shaft $A_{14}$) of the fourth arm 28d, that is subjected to the force from the elastic member (second gas spring 40), to rock around the center of rocking (second rotation axis $O_2$) for the same angle and in the same tilt direction as the tilt angle $\theta_Z$ of the floor. Thus, the floor tilt correcting mechanism 44 is a mechanism that readjusts the angle $\theta_D$ of item (3) to the same state as the one in which the operating microscope 10 is set on a level floor.

The following is a description of the function of the operating microscope 10 according to this embodiment.

In performing a surgical operation, the lens barrel portion 22 of the operating microscope 10 set on the level floor surface shown in FIG. 1A may be moved upward (or toward the topside of the drawing plane of FIG. 1B). In doing this, an operator holds the support arm 22a of the lens barrel portion 22 and moves the lens barrel portion 22 having the lens barrel 22b upward.

Thereupon, the third arm 28c rocks counterclockwise around the third rotation axis $O_3$, as shown in FIG. 2A. The shaft $A_{14}$, which serves as the fulcrum of the second gas spring 40, is situated on the axis $Z_3$ that connects the second rotation axis $O_2$ and the third rotation axis $O_3$. In this state, the angular moment $M_{A2}$, which is generated around the third rotation axis $O_3$ by the respective weights of the lens barrel portion 22, the second parallelogrammic link mechanism 20 that supports the same, etc., is given by $$M_{A2} = W_1 \cdot L_1 \cdot \cos \theta_{A2}.$$

This is a moment that is generated in the clockwise direction around the third rotation axis $O_3$.

On the other hand, the angular moment $M_{B2}$, which is generated around the third rotation axis $O_3$ by the spring force $F_{B2}$ of the first gas spring 36, is given by $$M_{B2} = F_{B2} \cdot (L_{S2}/L_{S1}) \cdot \cos \theta_{B2}.$$

This is a moment that is generated in the counterclockwise direction around the third rotation axis $O_3$.

Then, in moving the lens barrel portion 22 downward (or toward the bottom side of the drawing plane of FIG. 1B), the operator holds and moves the lens barrel portion 22 downward. Thereupon, the third arm 28c rocks clockwise around the third rotation axis $O_3$, as shown in FIG. 2B. In this state, the angular moment $M_{A3}$, which is generated around the third rotation axis $O_3$ by the respective weights of the lens barrel portion 22, the second parallelogrammic link mechanism 20 that supports the same, etc., is given by $$M_{A3} = W_1 \cdot L_1 \cdot \cos \theta_{A3}.$$

This is a moment that is generated in the clockwise direction around the third rotation axis $O_3$.

On the other hand, the angular moment $M_{B3}$, which is generated around the third rotation axis $O_3$ by the spring force $F_{B3}$ of the first gas spring 36, is given by $$M_{B3} = F_{B3} \cdot (L_{S2}/L_{S1}) \cdot \cos \theta_{B3}.$$

This is a moment that is generated in the counterclockwise direction around the third rotation axis $O_3$.

Then, in moving the lens barrel portion 22 to its original position, the operator holds and moves the lens barrel portion 22 upward. Thereupon, the third arm 28c rocks counterclockwise around the third rotation axis $O_3$, as shown in FIG. 1B. In this state, the angular moment that is generated around the third rotation axis $O_3$ by the respective weights of the lens barrel portion 22, the second parallelogrammic link mechanism 20 that supports the same, etc. is given by $$M_{A1} = W_1 \cdot L_1 \cdot \cos \theta_{A1}.$$

This is a moment that is generated in the clockwise direction around the third rotation axis $O_3$.

On the other hand, the angular moment $M_{B1}$, which is generated around the third rotation axis $O_3$ by the spring force $F_{B1}$ of the first gas spring 36, is given by $$M_{B1} = F_{B1} \cdot (L_{S2}/L_{S1}) \cdot \cos \theta_{B1}.$$

This is a moment that is generated in the counterclockwise direction around the third rotation axis $O_3$.

The rotating shafts $A_9$, $A_{11}$ and $A_{12}$ are located relatively to the rotating shaft $A_{10}$ and the first gas spring 36 is selected so that the angular moments $M_{A2}$ and $M_{B2}$ are substantially equal to each other in the state shown in FIG. 2A. Likewise, the rotating shafts $A_9$, $A_{11}$ and $A_{12}$ are located relatively to the rotating shaft $A_{10}$ and the first gas spring 36 is selected so that the angular moments $M_{A3}$ and $M_{B3}$ are substantially equal to each other in the state shown in FIG. 2B and that the angular moments $M_{A1}$ and $M_{B1}$ are so in the state shown in FIG. 1B. Thus, the third arm 28c rests around the third rotation axis $O_3$.

When the lens barrel portion 22 is moved in the vertical direction, therefore, the lens barrel portion 22 is balanced so that it can rest in any posture.

Then, in moving backward (or to the left of the drawing plane of FIG. 1B) the lens barrel portion 22 of the operating microscope 10 of FIG. 1A that is set on the level floor surface, the operator holds and moves the lens barrel portion 22 backward. Thereupon, the fourth arm 28d rocks counterclockwise around the second rotation axis $O_2$ as shown in FIG. 3A.

The rotating shaft $A_{14}$, which serves as the fulcrum of the second gas spring 40, is situated on the axis $Z_3$ that connects the second and third rotation axes $O_2$ and $O_3$. In this state, the angular moment $M_{C2}$, which is generated around the second rotation axis $O_2$ by the respective weights of the lens barrel portion 22, the second parallelogrammic link mechanism 20 that supports the same, etc., is given by $$M_{C2} = (W_2 \cdot L_2 + W_3 \cdot L_3) \sin \theta_{C2}.$$

This is a moment that is generated in the counterclockwise direction around the second rotation axis $O_2$.

On the other hand, the angular moment $M_{D2}$, which is generated around the second rotation axis $O_2$ by the spring force $F_{D2}$ of the second gas spring 40, is given by $$M_{D2} = F_{D2} \cdot L_4 \cdot \cos \theta_{D2}.$$

This is a moment that is generated in the clockwise direction around the second rotation axis $O_2$.

Then, in moving the lens barrel portion 22 forward (or to the right of the drawing plane of FIG. 1B), the operator holds and moves the lens barrel portion 22 forward. Thereupon, the fourth arm 28d rocks clockwise around the second rotation axis $O_2$, as shown in FIG. 3B. In this state, the angular moment $M_{C3}$, which is generated around the second rotation axis $O_2$ by the respective weights of the lens barrel portion 22, the second parallelogrammic link mechanism 20 that supports the same, etc., is given by $$M_{C3} = (W_2 \cdot L_2 + W_3 \cdot L_3) \sin \theta_{C3}.$$

This is a moment that is generated in the clockwise direction around the second rotation axis $O_2$.

On the other hand, the angular moment $M_{D3}$, which is generated around the second rotation axis $O_2$ by the spring force $F_{D3}$ of the second gas spring 40, is given by $$M_{D3} = F_{D3} \cdot L_4 \cdot \cos \theta_{D3}.$$

This is a moment that is generated in the counterclockwise direction around the second rotation axis $O_2$.

Then, in moving the lens barrel portion 22 to its original position, the operator holds and moves the lens barrel portion 22 backward. Thereupon, the fourth arm 28d rocks counterclockwise around the second rotation axis $O_2$, as shown in FIG. 1B. In this state, the angular moment $M_{C1}$, which is generated around the second rotation axis $O_2$ by the respective weights of the lens barrel portion 22, the first and second parallelogrammic link mechanisms 16 and 20 that supports the same, etc., is given by $$M_{C1}=(W_2 \cdot L_2+W_3 \cdot L_3)\sin\theta_{C1}.$$

Since the angle $\theta_{C1}$ is 0°, this moment $M_{C1}$ is 0.

On the other hand, the angular moment $M_{D1}$, which is generated around the second rotation axis $O_2$ by the spring force $F_{D1}$ of the second gas spring 40 is given by $$M_{D1}=F_{D1} \cdot L_4 \cdot \cos\theta_{D1}.$$

Since the angle $\theta_{D1}$ is 90°, this moment $M_{D1}$ is 0.

The rotating shafts $A_{13}$ and $A_{14}$ are located relatively to the second rotation axis $O_2$ and the second gas spring 40 is selected so that the angular moments $M_{C2}$ and $M_{D2}$ are substantially equal to each other in the state shown in FIG. 3A. Likewise, the rotating shafts $A_{13}$ and $A_{14}$ are located relatively to the second rotation axis $O_2$ and the second gas spring 40 is selected so that the angular moments $M_{C3}$ and $M_{D3}$ are substantially equal to each other in the state shown in FIG. 3B and that the angular moments $M_{C1}$ and $M_{D1}$, which are both 0 (zero), are so in the state shown in FIG. 1B. Thus, the fourth arm 28d rests around the second rotation axis $O_2$.

When the lens barrel portion 22 is moved back and forth, therefore, the lens barrel portion 22 is balanced so that it can rest in any posture.

The following is a description of a case where the operating microscope 10 is located on an inclined floor surface.

In FIG. 4A, the operating microscope 10 is located on the floor surface that is inclined at the tilt angle $\theta_Z$ with the fourth arm 28d kept in the vertical posture so that its front (on the side of the lens barrel portion 22) and back are on the higher and lower sides, respectively. In this state, the angular moment $M_{C4}$, which is generated around the second rotation axis $O_2$ by the respective weights of the lens barrel portion 22, the first and second parallelogrammic link mechanisms 16 and 20 that support the same, etc., is given by $$M_{C4}=(W_2 \cdot L_2+W_3 \cdot L_3)\sin\theta_{C4}.$$

Since the angle $\theta_{C4}$ is 0°, this moment $M_{C4}$ is 0. It is equal to the angular moment $M_{C1}$ that is generated when the floor is not inclined, as shown in FIG. 1B, that is, when the operating microscope 10 is located on a horizontal plane.

On the other hand, the angular moment $M_{D4}$, which is generated around the second rotation axis $O_2$ by the spring force $F_{D4}$ of the second gas spring 40 is given by $$M_{D4}=F_{D4} \cdot L_4 \cdot \cos\theta_{D4}.$$

This is a moment that is generated in the clockwise direction around the second rotation axis $O_2$.

Since the angle $\theta_{C4}$ is 90° in FIG. 1B, the angular moment $M_{D1}$ is 0. The position of the rotating shaft $A_{13}$ is rocked for the tilt angle $\theta_Z$ around the second rotation axis $O_2$, and the angle $\theta_{D4}$ is smaller than 90°, so that the angular moment $M_{D4}$ is not 0.

This is a moment that is generated in the counterclockwise direction around the second rotation axis $O_2$. While the angular moment $M_{C4}$ is 0, there exists the angular moment $M_{D4}$ that is generated in the counterclockwise direction around the second rotation axis $O_2$. Thus, the fourth arm 28d tilts backward (or away from the lens barrel portion 22) around the second rotation axis $O_2$, and the lens barrel portion 22 also naturally moves backward.

In order to correct this imbalance caused by the tilt $\theta_Z$ of the floor, the slider 52 shown in FIG. 1C is moved to the left for the movement amount $X_1$ from the axis $Z_3$ that connects the second rotation axis $O_2$ and the third rotation axis $O_3$, as shown in FIG. 5A.

If the movement amount $X_1=L_4 \cdot \sin\theta_Z$ is given here, the rotating shaft $A_{14}$ is situated in a position such that it is rocked counterclockwise by a margin corresponding to the tilt angle $\theta_Z$ around the second rotation axis $O_2$. In this state, the angular moment $M_{C6}$, which is generated around the second rotation axis $O_2$ by the respective weights of the lens barrel portion 22, the first and second parallelogrammic link mechanisms 16 and 20 that support the same, etc., is given by $$M_{C6}=(W_2 \cdot L_2+W_3 \cdot L_3)\sin\theta_{C6}.$$

Since the angle $\theta_{C6}$ is 0°, the angular moment $M_{C6}$ is 0.

On the other hand, the angular moment $M_{D5}$, which is generated around the second rotation axis $O_2$ by the spring force of the second gas spring 40 is given by $$M_{D5}=F_{D6} \cdot L_4 \cdot \cos\theta_{D6}.$$

Since the angle $\theta_{D6}$ is 90°, this moment $M_{D5}$ is 0. Since the angular moment $M_{C6}=M_{D6}=0$ is given, the moment around the second rotation axis $O_2$ is 0, so that the fourth arm 28d rests. Thus, the lens barrel portion 22 is also balanced and rests.

FIG. 4B illustrates a state in which the fourth arm 28d is rocked counterclockwise for the tilt angle $\theta_Z$ around the second rotation axis $O_2$ after it is naturally moved from the state of FIG. 4A. In this state, the angular moment $M_{C5}$, which is generated around the second rotation axis $O_2$ by the respective weights of the lens barrel portion 22, the first and second parallelogrammic link mechanisms 16 and 20 that support the same, etc., is given by $$M_{C5}=(W_2 \cdot L_2+W_3 \cdot L_3)\sin\theta_Z(\theta_{C5}=\theta_Z).$$

This is a moment that is generated in the counterclockwise direction around the axis $O_2$.

On the other hand, the angular moment $M_{D5}$, which is generated around the second rotation axis $O_2$ by the spring force $F_{D5}$ of the second gas spring 40, is given by $$M_{D5}=F_{D5} \cdot L_4 \cdot \cos\theta_{D5}.$$

Since the angle $\theta_{D5}$ is 90°, the angular moment $M_{D5}$ is 0.

While the angular moment $M_{D5}$ is 0, there exists the angular moment $M_{C5}$ that is generated in the counterclockwise direction around the second rotation axis $O_2$. Thus, the fourth arm 28d tilts backward (or away from the lens barrel portion 22) around the second rotation axis $O_2$ and the lens barrel portion 22 also naturally moves backward.

If the operating microscope 10 is located on the floor inclined in this manner, the fourth arm 28d naturally moves around the second rotation axis $O_2$ to the lower side. If this state is entered, the slider 52 is moved to the left in FIG. 1C by rotating counterclockwise the rotary knob 60 of the floor tilt correcting mechanism 44 shown in FIG. 1C.

Thus, in order to correct this imbalance caused by the tilt $\theta_Z$ of the floor, the slider 52 shown in FIG. 1C is moved along the shaft member 50 so that the fourth arm 28d is rotated counterclockwise for the tilt angle $\theta_Z$ around the second rotation axis $O_2$ from the state shown in FIG. 4B. In this state, the angular moment $M_{C7}$, which is generated around the second rotation axis $O_2$ by the respective weights of the lens barrel portion 22, the first and second parallelogrammic link mechanisms 16 and 20 that support the same, etc., is given by $$M_{C7}=(W_2 \cdot L_2+W_3 \cdot L_3)\sin\theta_Z(\theta_{C7}=\theta_Z).$$

This is a moment that is generated in the counterclockwise direction around the axis $O_2$.

On the other hand, the angular moment $M_{D7}$, which is generated around the second rotation axis $O_2$ by the spring force of the second gas spring 40, is given by $$M_{D7}=F_{D7} \cdot L_4 \cdot \cos\theta_{D7}.$$

This is a moment that is generated in the counterclockwise direction around the second rotation axis $O_2$. It has a magnitude such that it cancels a weight moment that is generated when the fourth arm 28d of the system set on a level floor is inclined counterclockwise at the tilt angle $\theta_Z$. When the angular moments $M_{C7}$ and $M_{D7}$ are balanced with each other, therefore, the fourth arm 28d rests, and the lens barrel portion 22 is also balanced and rests.

In actual adjustment operation, the movement amount $X_1$ need not be precisely calculated, and the indexes 62a and 62b shown in FIG. 1A are aligned with each other to see if the fourth arm 28d tilts backward or forward with respect to the post 14. If the fourth arm 28d tilts backward, the rotary knob 60 of the floor tilt correcting mechanism 44 should only be rotated counterclockwise so that the fourth arm 28d rests. If the fourth arm 28d tilts forward, the rotary knob 60 should only be rotated clockwise in a like manner.

The position where the fourth arm 28d rests is a position where the movement amount $X_1$ equals $L_4 \cdot \sin\theta_Z$.

The center of gravity of the post 14 is situated right over the first rotation axis $O_1$. Therefore, the post 14 is hardly influenced by the inclination of the floor.

On the other hand, the respective centers of gravity of the first and second parallelogrammic link mechanisms 16 and 20 are not situated right over the first rotation axis $O_1$ but are located in separate positions. Thus, the first and second parallelogrammic link mechanisms 16 and 20 are influenced by the inclination of the floor.

The post 14 is heavier enough than the first and second parallelogrammic link mechanisms 16 and 20. Therefore, the center of gravity of the entire operating microscope 10 that combines the first and second parallelogrammic link mechanisms 16 and 20 and the post 14 is situated near the first rotation axis $O_1$. Accordingly, the operating microscope 10 is easily influenced by the inclination of the floor, so that the balance around the first rotation axis $O_1$ need not be adjusted.

Described above in connection with this embodiment is the function for correcting the imbalance that is caused by the inclination of the floor as the first fulcrum $A_{14}$ attached to the first parallelogrammic link mechanism 16 (horizontal motion arm) is moved with respect to the fourth arm 28d. Alternatively, however, the imbalance may be corrected by moving the second fulcrum $A_{13}$ in the post 14 with respect to the post 14.

According to the operating microscope 10 of this embodiment, as described above, the following effect can be obtained.

The position of the fulcrum (shaft $A_{14}$) of the second gas spring 40 attached to the fourth arm 28d is located so that it can be moved in a direction substantially perpendicular to the axis $Z_3$ of the fourth arm 28d. By doing this, the angle $\theta_D$ between the direction of action of the second gas spring 40 and the axis $Z_4$ that extends from the center of rocking of the fourth arm 28d (second rotation axis $O_2$) to the fulcrum (shaft $A_{14}$) of the second gas spring 40 can be readjusted to the same conditions for the level floor setting state. Accordingly, there may be provided the operating microscope 10 that can be leveled by a compact structure that can be adjusted more easily than a conventional leveling mechanism. Thus, there may be provided the operating microscope 10 that can be easily balanced by a simple mechanism even when it is set on an inclined floor as well as when it is set on a level floor surface.

A second embodiment will now be described with reference to FIGS. 6A to 6C. This embodiment is a modification of the first embodiment, so that like numerals are used to designate the same members as those described in connection with the first embodiment, and a detailed description of those members is omitted.

Figure 6A:
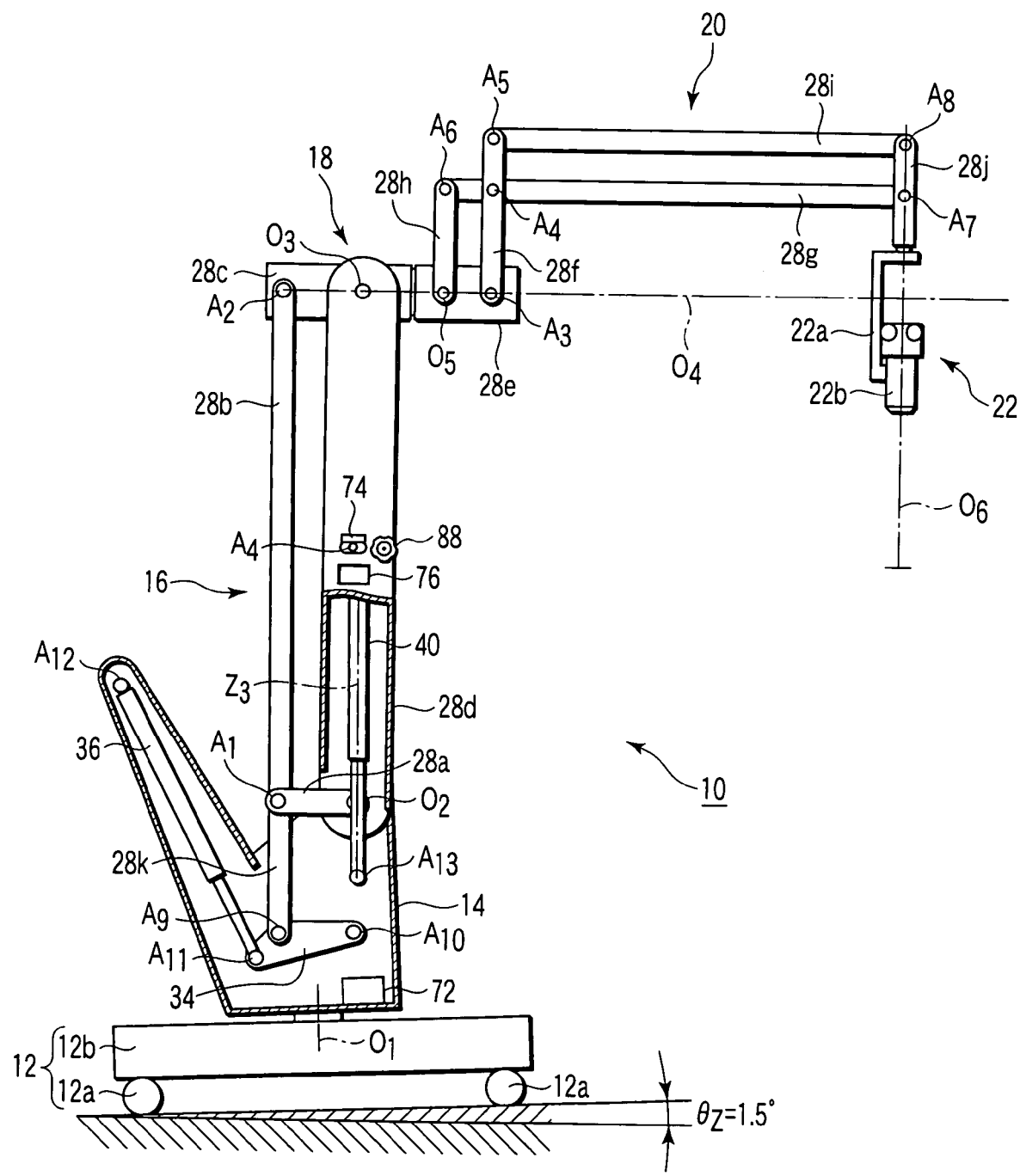
FIG. 6A is a front view, partially in section, showing an operating microscope according to a second embodiment and illustrating a state in which the operating microscope is located on an inclined floor.

As shown in FIG. 6A, a tilt angle sensor 72 as a tilt angle detecting mechanism for detecting the tilt angle of the floor surface in a direction perpendicular to the second rotation axis $O_2$ is located in, for example, a bottom portion in the post 14.

Figure 6B:
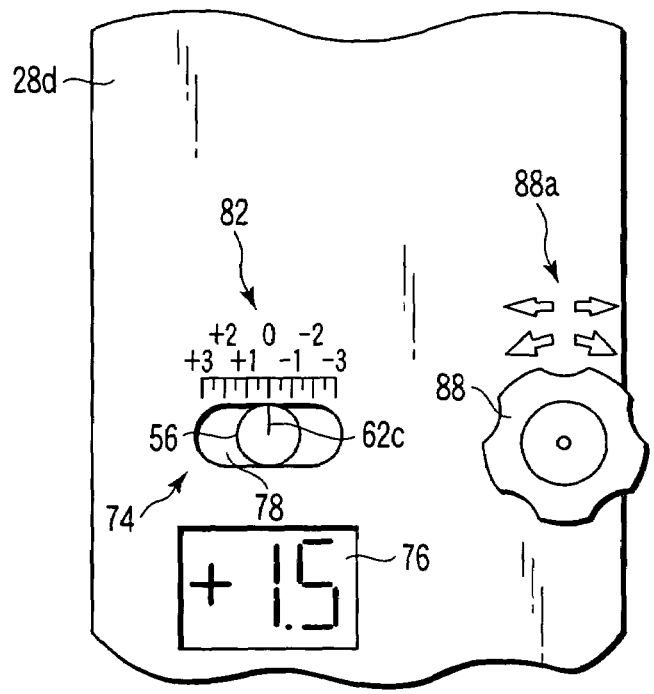
FIG. 6B is a schematic view showing a tilt angle detecting mechanism and a tilt angle display mechanism of the operating microscope according to the second embodiment are provided on a fourth arm.

As shown in FIG. 6B, the fourth arm 28d is provided with a window portion 74 for use as a fulcrum position viewing portion and an LCD 76 as a tilt angle display mechanism. The window portion 74 allows the position of the shaft portion 56 or the fulcrum (shaft $A_{14}$) of the second gas spring 40 to be visually recognized from outside an operating microscope 10. The LCD 76 displays angle information that is detected by the aforesaid tilt angle sensor 72.

The window portion 74 is provided with a transparent cover 78, which prevents dirt or dust from getting into the fourth arm 28d and hindering the movement of the shaft portion 56. An index 62c is printed on the shaft portion 56.

Provided over the window portion 74 is a scale 82 for use as a contrastive member for a necessary fulcrum movement amount for the correction of the tilt angle of the floor surface. The LCD 76 is located under the window portion 74 and displays the tilt angle of the floor surface in the direction perpendicular to the second rotation axis $O_2$ which is detected by the tilt angle sensor 72. This displayed numerical value indicates that the front side (right-hand side in FIG. 6A) is higher if it is + (positive), and indicates that the rear side (left-hand side in FIG. 6B) is higher if it is − (negative). The numerical value of the scale 82 is calculated according to the calculation formula, movement amount $X_1=L_4 \cdot \sin\theta_Z$, described in connection with the first embodiment.

Figure 6C:
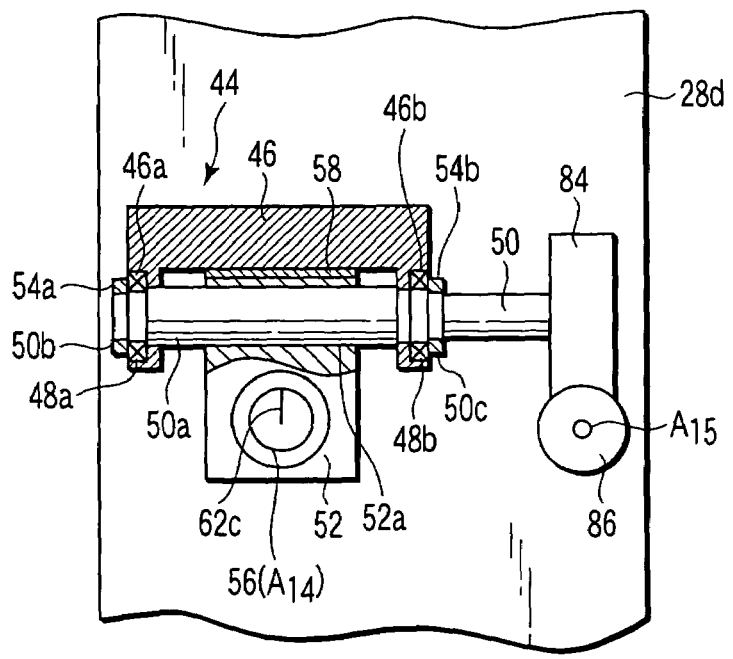
FIG. 6C is a schematic view showing a floor tilt correcting mechanism of the operating microscope according to the second embodiment.

FIG. 6C shows the floor tilt correcting mechanism 44 in the fourth arm 28d shown in FIG. 6B. A right-handed worm wheel 84 is fixed to the right-hand end portion (on the side of the lens barrel portion 22) of the shaft member 50 on which the rotary knob 60 is provided in FIG. 1C described in connection with the first embodiment. A right-handed worm 86 is engaged with the worm wheel 84.

The worm 86 is supported for rotation around a shaft $A_{15}$ by a bearing (not shown). The worm 86 is drawn out through a hole that is formed in the fourth arm 28d. As shown in FIG. 6B, a knob 88 is provided on an end portion of the worm 86. Located near the knob 88 is a display portion 88a that indicates the direction of movement of the index 62c based on the direction of rotation of the knob 88.

The following is a description of a function for correcting the imbalance of the first parallelogrammic link mechanism 16 that is caused by the inclination of the floor as a surgical operation is performed using the operating microscope 10 shown in FIG. 6A.

The operator views a figure that is detected by the tilt angle sensor 72 and displayed on the LCD 76 for use as the tilt angle display mechanism of the fourth arm 28d shown in FIG. 6B.

As shown in FIG. 6B, "+1.5" is displayed on the LCD 76, and it indicates that the front side (right-hand side in FIG. 6A) and the rear side (left-hand side in FIG. 6B) of the operating microscope 10 are higher and lower, respectively, with respect to the inclined floor. The operator is expected to move the index 62c so that it indicates the numerical value (+1.5) displayed on the LCD 76. In doing this, the operator should only move the slider 52 to the left in FIG. 6C. Thus, the knob 88 is rotated counterclockwise around the shaft $A_{15}$ with reference to the display portion 88a.

The worm 86 is fixed to the knob 88. As the knob 88 is rotated counterclockwise around the shaft $A_{15}$, the worm wheel 84 that is engaged with the worm 86 also rotates counterclockwise. The shaft member 50 that is fixed to the worm wheel 84 also rotates counterclockwise, whereupon the slider 52 moves to the left in the FIG. 6C. As the position of the shaft portion 56 (shaft $A_{14}$) that is fixed to the slider 52 thus moves to the position "+1.5" of the scale 82, the imbalance of the first parallelogrammic link mechanism 16 that is caused by the inclination of the floor is corrected.

According to this embodiment, as described above, the following effect can be obtained. A description of the effect described in connection with the first embodiment is omitted.

The operator need not confirm the direction, forward or backward, in which fourth arm 28d (horizontal motion arm) tilts, and can balance the operating microscope 10 merely by rotating the knob 88 according to the displayed numerical value. If the operating microscope 10 is set on an inclined floor, therefore, the balance can be adjusted with ease.

A third embodiment will now be described with reference to FIGS. 7A and 7B. This embodiment is a modification of the second embodiment, so that like numerals are used to designate the same members as those described in connection with the second embodiment, and a detailed description of those members is omitted.

This embodiment is configured so that the shaft portion 56 (shaft $A_{14}$) that is moved as the operator operates the knob 88 according to the second embodiment can be automatically moved by a movement control mechanism that includes a motor.

Figure 7A:
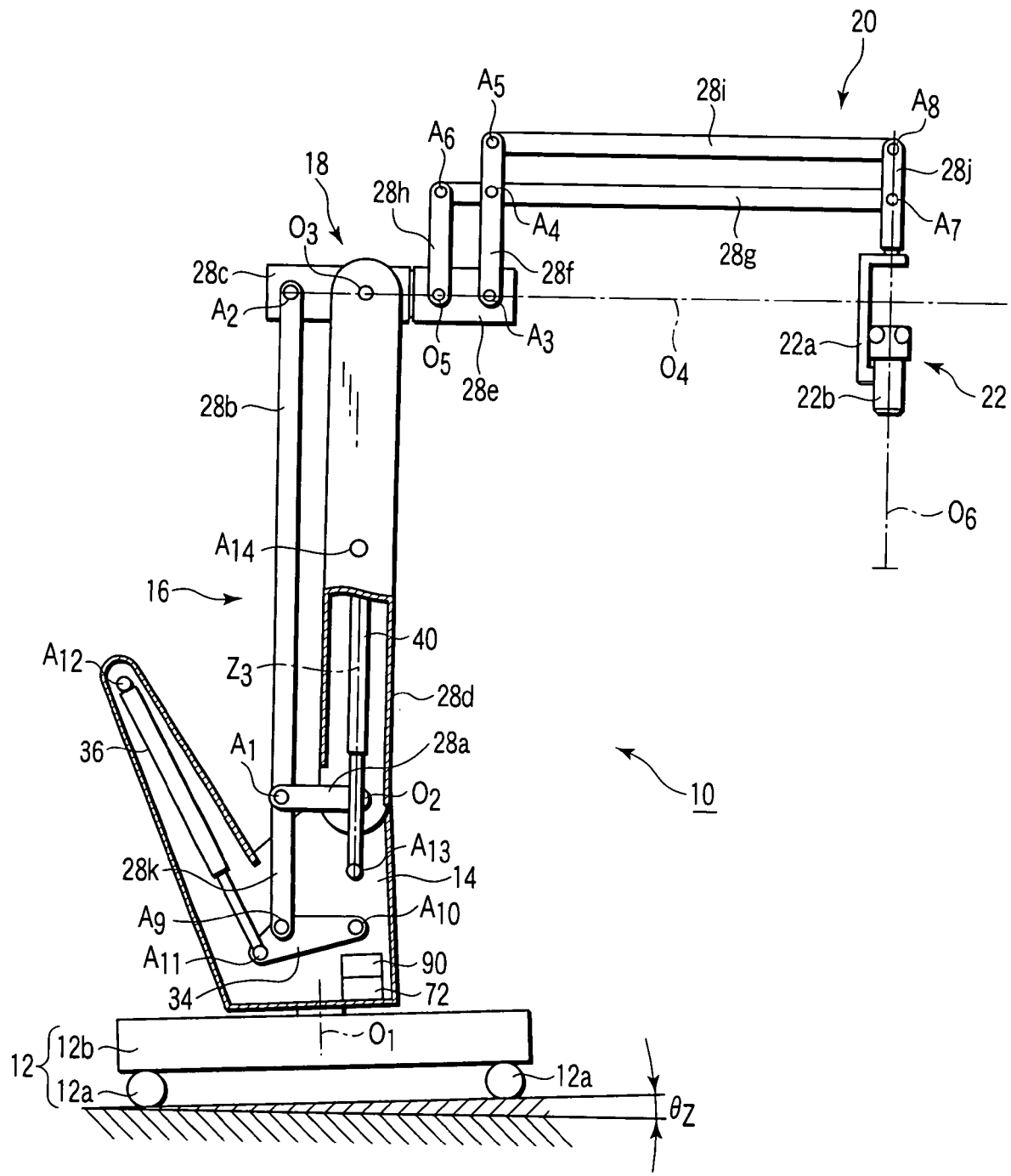
FIG. 7A is a front view, partially in section, showing an operating microscope according to a third embodiment and illustrating a state in which the operating microscope is located on an inclined floor.

Located in the post 14, as shown in FIG. 7A, is a motor drive circuit 90 that drives a motor 96 (mentioned later) in response to an output from the tilt angle sensor 72.

Figure 7B:
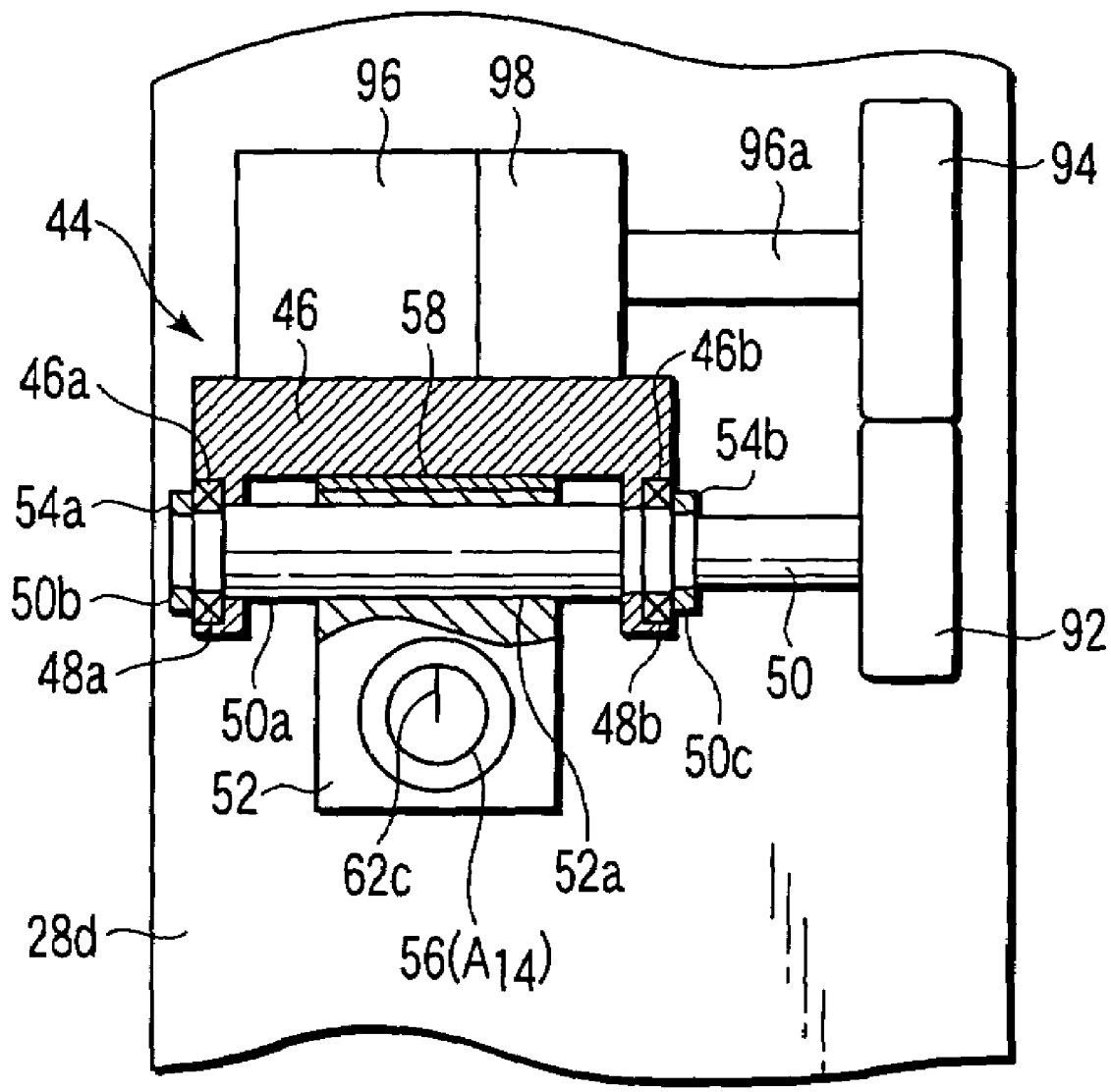
FIG. 7B is a schematic view showing a floor tilt correcting mechanism of the operating microscope according to the third embodiment.

FIG. 7B shows the floor tilt correcting mechanism 44 in the fourth arm 28d. A spur gear 92 is fixed to the right-hand end portion of the shaft member 50. The spur gear 92 is in mesh with a gear 94. The motor 96 is connected to the gear 94 through an encoder 98 that detects the rotational angle of a motor drive shaft 96a.

The motor drive circuit 90 shown in FIG. 7A compares the tilt angle of the floor detected by the tilt angle sensor 72 and the rotational angle of the drive shaft 96a of the motor 96 detected by the encoder 98, and drives motor 96 to move and rotate the slider 52 to a balanced position. Thus, the motor drive circuit 90, motor 96, and encoder 98 constitute the movement control mechanism.

The following is a description of a function for correcting the imbalance of the first parallelogrammic link mechanism 20 that is caused by the inclination of the floor as a surgical operation is performed using an operating microscope 10 shown in FIG. 7A.

The tilt angle is detected by the tilt angle sensor 72 that is provided in the post 14. The rotational angle of the drive shaft 96a of the motor 96 is detected by the encoder 98 that is provided in the fourth arm 28d.

The motor drive circuit 90 makes a comparison to see if the tilt angle of the floor surface and the rotational angle of the drive shaft 96a comply with previously calculated balance conditions, and drives the motor 96 to a position where the conditions are met. Thus, the slider 52 and the shaft portion 56 (shaft $A_{14}$) are moved as the motor moves so that the tilt angle of the floor surface and the rotational angle of the drive shaft 96a comply with the balance conditions. Thereupon, the imbalance of the first parallelogrammic link mechanism 16 that is caused by the inclination of the floor is automatically corrected.

According to the operating microscope 10 of this embodiment, as described above, the following effect can be obtained. A description of the effects described in connection with the first and second embodiments is omitted.

Since the imbalance of the horizontal motion arm caused by the inclination of the floor is automatically corrected based on the detected tilt angle of the floor, the necessity of balance adjustment operation can be obviated. Thus, the operating microscope 10 can be operated more easily in a balanced state.

A fourth embodiment will now be described with reference to FIGS. 8A and 8B. This embodiment is a modification of the first embodiment, so that like numerals are used to designate the same members as those described in connection with the first embodiment, and a detailed description of those members is omitted.

In general, the spring force of a gas spring tends to increase as its temperature rises and to lower as its temperature drops. This embodiment is configured so that fluctuations of the spring force of the second gas spring 40 attributable to temperature change can be corrected with ease.

Figure 8A:
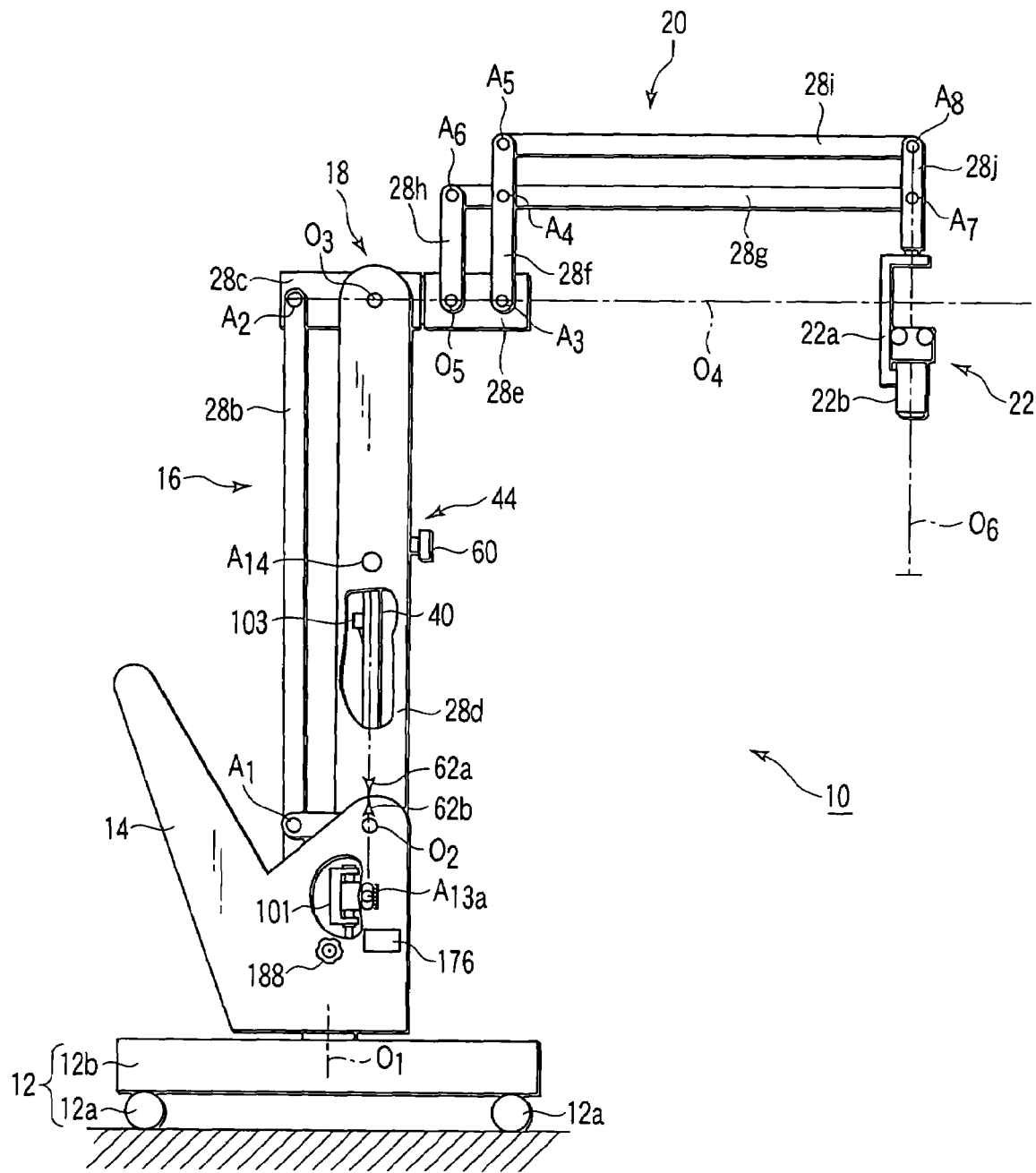
FIG. 8A is a schematic front view, partially in section, showing an operating microscope according to a fourth embodiment.

Located in the post 14, as shown in FIG. 8A, is a spring force correcting mechanism (temperature correcting mechanism) 101, which rockably supports the lower end portion (shaft $A_{13a}$) of the second gas spring 40. The second gas spring 40 in the fourth arm 28d is provided with a temperature sensor 103. The temperature sensor 103 can detect the temperature of the second gas spring 40.

FIG. 8B enlargedly shows the spring force correcting mechanism 101 in the post 14. The spring force correcting mechanism 101 is provided with substantially the same system as the floor tilt correcting mechanism 44 described in connection with the first embodiment. Specifically, the spring force correcting mechanism 101 includes a seat 146 fixed to the post 14, a pair of bearings (not shown), a shaft member 150, and a slider 152.

Seat holes (not shown) are formed in an extended portion (projected lug portion) that extend individually downward from the opposite end portions of the seat 146. The aforesaid bearings are located individually in these seat holes. The slider 152 is located between the bearings. It is movable along the longitudinal axis of the shaft member 150 that has a right-handed male thread portion 150a on its outer peripheral surface. The slider 152 has a female thread portion (not shown) on its inner peripheral surface that threadedly mates with the male thread portion 150a.

The bearings and the slider 152 are arranged so that the shaft member 150 is rotatable therein. The longitudinal axis of the shaft member 150 is located extending in the vertical direction, for example. Male thread portions (not shown) are formed on the outer peripheral surface of the shaft member 150, corresponding individually to positions in which the bearings are arranged. Retaining rings 154a and 154b are threadedly fitted on the male thread portions, individually, whereby the shaft member 150 is prevented from slipping off the bearings.

The slider 152 is provided with a shaft portion 156 (shaft $A_{13a}$) that supports the lower end portion of the second gas spring 40 for rocking motion. The seat 146 and the slider 152 are arranged so that their respective flat portions face each other, and a flat resin plate (not shown) is fixed to the flat portion of the slider 152. If the shaft member 150 rotates, therefore, the seat 146 and the slider 152 are prevented from rotating relatively to each other, and the slider 152 moves along the longitudinal axis of the shaft member 150 as the shaft member 150 rotates.

A worm wheel 184 is provided on the lower end portion of the shaft member 150. A worm 186 is engaged with the worm wheel 184. The worm 186 is supported for rotation around a shaft $A_{16}$ by a bearing (not shown). The worm 186 is drawn out through a hole that is formed in the post 14. As shown in FIG. 8A, a rotary knob 188 is provided on an end portion of the worm 186.

The spring force correcting mechanism 101 is a mechanism configured so that the shaft $A_{13a}$ can be raised or lowered by rotating the rotary knob 188, whereby the spring force of the second gas spring 40 can be varied (or corrected) when the temperature of the second gas spring 40 changes. The post 14 is provided with a window portion 174 for use as a fulcrum position viewing portion and an LCD 176 as a temperature display mechanism. The window portion 174 allows the position of the fulcrum (shaft $A_{13a}$) of the second gas spring 40 to be visually recognized from outside an operating microscope 10. The LCD 176 displays temperature information that is detected by the aforesaid temperature sensor 103.

The position of the shaft $A_{13a}$ can be recognized through the window portion 174. The window portion 174 is provided with a transparent cover 178, and the shaft $A_{13a}$ is provided with an index 62d. Provided on the right-hand side of the window portion 174 is a scale 182 for use as a contrastive index for a necessary fulcrum movement amount for the correction of the temperature of the second gas spring 40. The displayed numerical value of the scale 182 is one that is previously calculated according to the temperature characteristic of the second gas spring 40 and the location of the shaft.

The LCD 176 is provided under the window portion 174 and displays the temperature of the second gas spring 40 detected by the temperature sensor 103. Located near the rotary knob 188 is a display portion (not shown) that displays the direction in which the index 62d moves as the rotary knob 188 rotates.

The following is a description of a function for correcting the imbalance of the first parallelogrammic link mechanism 16 that is caused by the temperature change of the second gas spring 40 as a surgical operation is performed using the operating microscope 10 shown in FIG. 8A.

The operator views a figure that is detected by the temperature sensor 103 and displayed on the LCD 176 for use as the temperature display mechanism of the fourth arm 28d shown in FIG. 8B.

As shown in FIG. 8B, "22.5" is displayed on the LCD 176. The operator is expected to move the index 62d so that it indicates the numerical value displayed on the LCD 176. In doing this, the operator should only move the slider 152 upward as in FIG. 8B, so that he/she rotates the rotary knob 188 counterclockwise around the shaft $A_{16}$ with reference to the display portion. The worm 186 is fixed to the rotary knob 188. As the rotary knob 88 is rotated counterclockwise around the shaft $A_{16}$, the worm wheel 184 that is engaged with the worm 186 also rotates counterclockwise. The shaft member 150 that is fixed to the worm wheel 184 also rotates counterclockwise, whereupon the slider 152 moves upward as in the FIG. 8B. As the position of the shaft portion 156 (shaft $A_{13a}$) that is fixed to the slider 152 thus moves to the position "+22.5" of the scale 182, the imbalance of the first parallelogrammic link mechanism 16 that is caused by the temperature change of the second gas spring 40 is corrected.

According to this embodiment, as described above, the following effect can be obtained. A description of the effect described in connection with the first embodiment is omitted.

If the spring force (reaction force) of the second gas spring 40 is changed owing to the temperature change of the second gas spring 40, that force can be corrected. Thus, the fourth arm 28d (horizontal motion arm) can be balanced with ease.

Although the correction is made by manually rotating the rotary knob 188 according to this embodiment, the mechanism described in connection with the third embodiment may be used for automatic correction. By doing this, the horizontal motion arm can be balanced more easily.

A fifth embodiment will now be described with reference to FIGS. 9A to 11B. This embodiment is a modification of the first embodiment, so that like numerals are used to designate the same members as those described in connection with the first embodiment, and a detailed description of those members is omitted.

Figure 9A:
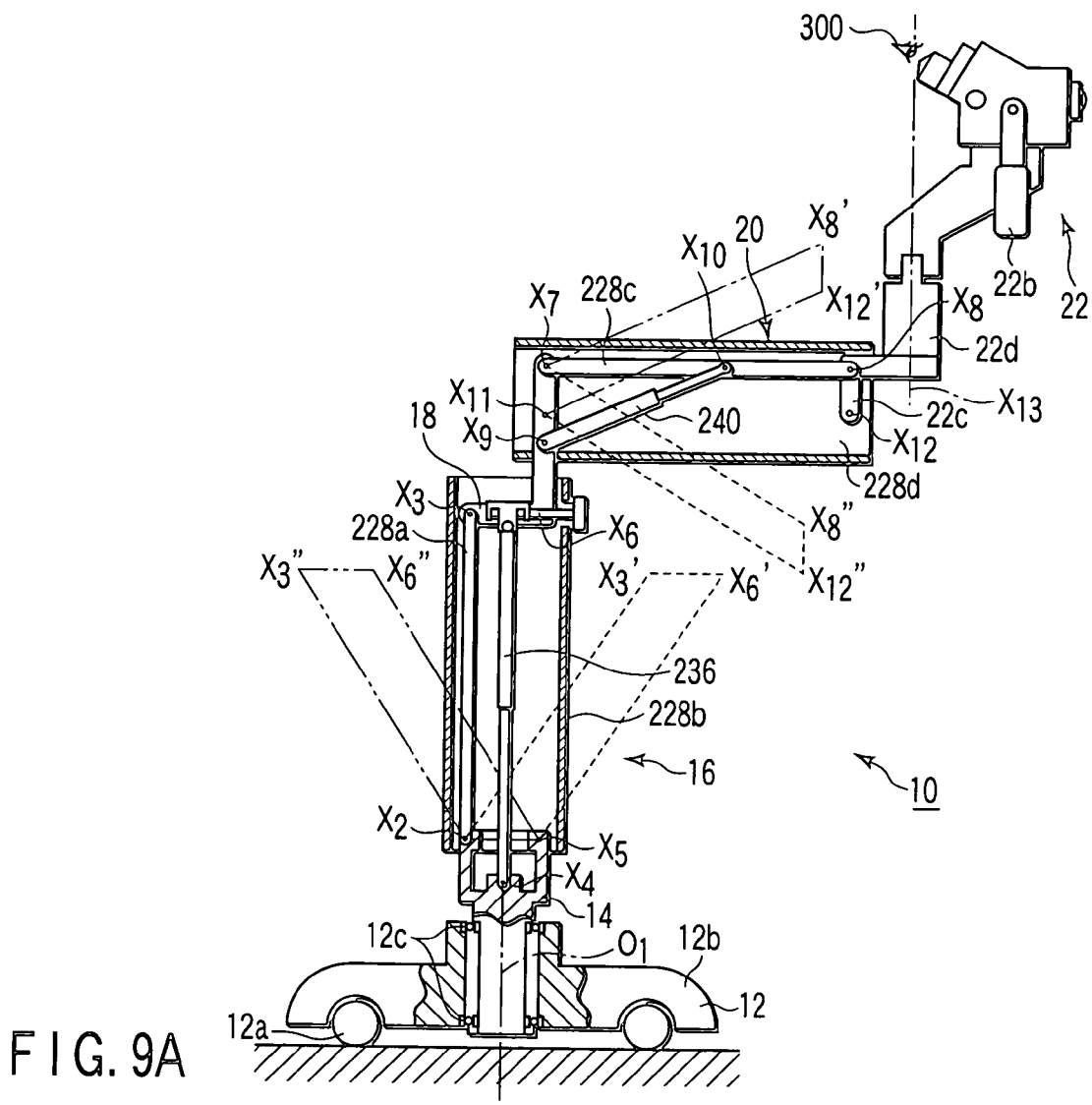
FIG. 9A is a schematic front view, partially in section, showing an operating microscope according to a fifth embodiment.

As shown in FIG. 9A, an operating microscope 10 according to this embodiment comprises the base 12, arm seat (post) 14, first parallelogrammic link mechanism (horizontal motion arm) 16, L-shaped joint (link) 18, second parallelogrammic link mechanism (vertical motion arm) 20, and lens barrel portion 22.

The first rotating shaft $O_1$ that extends in the vertical direction is rotatably supported on the base body 12b of the base 12 by bearings 12c. The lower end portion of the arm seat 14 as the post is located on the first rotating shaft $O_1$ so as to be rotatable around the first rotating shaft $O_1$. The arm seat 14 supports the lower end portion of the first parallelogrammic link mechanism 16. The L-shaped joint 18 is located on the upper end portion of the first parallelogrammic link mechanism 16. One end portion of the second parallelogrammic link mechanism 20 is supported on the joint 18. The lens barrel portion 22 is supported on the other end portion of the second parallelogrammic link mechanism 20.

In this embodiment, the first and second parallelogrammic link mechanisms 16 and 20 are individually closed by themselves. Thus, the first and second parallelogrammic link mechanisms 16 and 20 have their respective structures that can be balanced independently.

The first parallelogrammic link mechanism 16 has first and second arms 228a and 228b and a first gas spring 236.

The lower end portion of the first arm 228a is connected to the upper end portion of the arm seat 14 by a second rotating shaft $X_2$ (first horizontal rotating shaft). The upper end portion of the first arm 228a is connected to one end portion of the L-shaped joint 18 by a third rotating shaft $X_3$.

The lower end portion of the first gas spring 236 is connected to the arm seat 14 by a fourth rotating shaft $X_4$ (second fulcrum). The fourth rotating shaft $X_4$ is supported on the lower end portion side of an axis that connects the second rotating shaft $X_2$ and a fifth rotating shaft $X_5$ (mentioned later) on the same height level at the upper end portion of the arm seat 14.

The floor tilt correcting mechanism 44 (see FIG. 9B) described in connection with the first embodiment is located between the one end portion and a bent portion of the L-shaped joint 18. The upper end portion of the first gas spring 236 is connected to the rotating shaft $A_{14}$ of the floor tilt correcting mechanism 44.

Thus, the first gas spring 236 is interposed between the arm seat 14 and the joint 18. The first gas spring 236 is provided as a compression spring (elastic member) that is prevented from buckling in the direction of an axis that connects the fourth rotating shaft $X_4$ and the rotating shaft $A_{14}$, of the floor tilt correcting mechanism 44. Thus, the first gas spring 236 generates a reaction force when it is subjected to a force in the direction of compression.

Figure 9B:
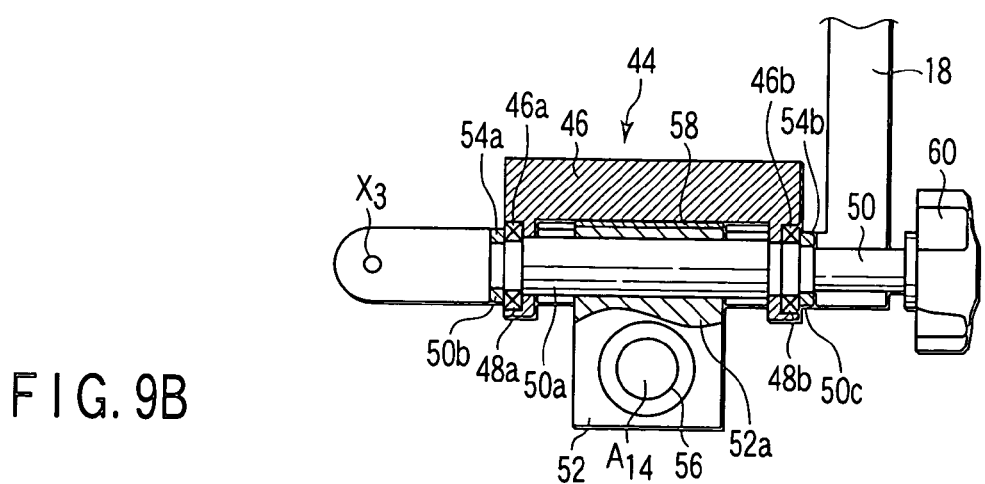
FIG. 9B is a schematic partial sectional view extractively showing a floor tilt correcting mechanism of the operating microscope shown in FIG. 9A in the operating microscope according to the fifth embodiment.

As shown in FIG. 9B, the floor tilt correcting mechanism 44 may be either mounted on the joint 18 or formed as a part of the L-shaped joint 18. Since the floor tilt correcting mechanism 44 has the same configuration as the floor tilt correcting mechanism 44 described in connection with the first embodiment, a description thereof is omitted.

As shown in FIG. 9A, the second arm 228b is formed substantially in the shape of a cylinder such that it can contain the first arm 228a and the first gas spring 236. The lower end portion of the second arm 228b is connected to the upper end portion of the arm seat 14 by the fifth rotating shaft $X_5$ (first horizontal rotating shaft). The upper end portion of the second arm 228b is connected by a sixth rotating shaft $X_6$ at the bent portion of the joint 18. Specifically, the second arm 228b is supported on the upper end portion of the arm seat 14 and the joint 18 by the fifth and sixth rotating shafts $X_5$ and $X_6$.

Thus, the first and second arms 228a and 228b, the first gas spring 236, the arm seat 14, the L-shaped joint 18, the rotating shafts $X_2$, $X_4$ and $X_5$ of the arm seat 14, and the rotating shafts $X_3$, $X_6$ and $A_{14}$ of the joint 18 constitute the horizontal motion arm as the first parallelogrammic link mechanism 16.

Figure 10A:
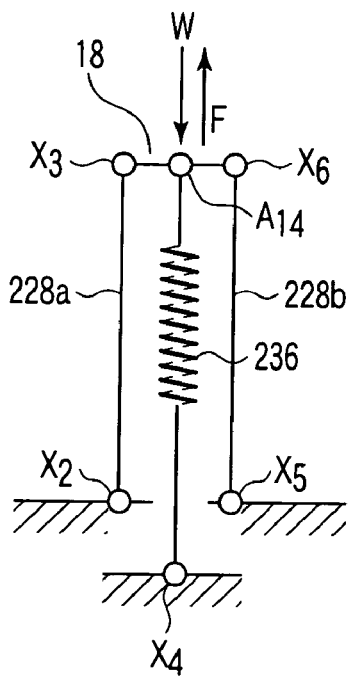
FIG. 10A is a schematic diagram of a first parallelogrammic link mechanism of the operating microscope according to the fifth embodiment.
Figure 10B:
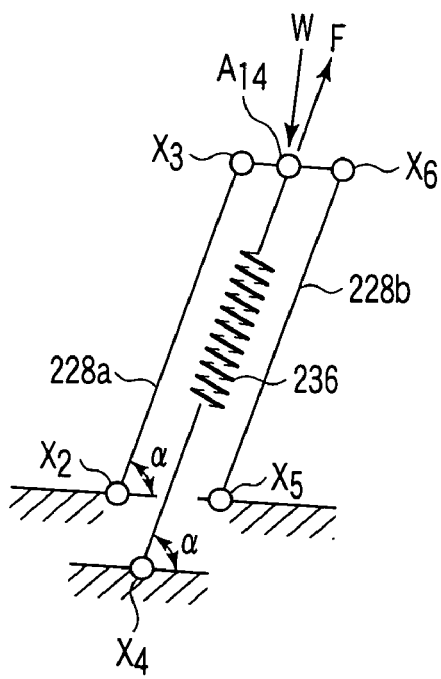
FIG. 10B is a schematic diagram illustrating a state obtained when the first parallelogrammic link mechanism of the operating microscope according to the fifth embodiment in the state shown in FIG. 10A is deformed.

FIGS. 10A and 10B show diagrams of the first parallelogrammic link mechanism 16. In this embodiment, as shown in FIGS. 10A and 10B, the first parallelogrammic link mechanism 16 is a closed system that can be balanced independently. For ease of illustration, the weight of each component member is regarded as negligible.

As shown in FIG. 10A, the first parallelogrammic link mechanism 16 is subjected to a gravity W based on the respective weights of the second parallelogrammic link mechanism 20 and the lens barrel portion 22 (especially the weight of the lens barrel portion 22). If the first parallelogrammic link mechanism 16 has the shape of a rectangle shown in FIG. 10A, the position where the gravity W is applied is situated on the first gas spring 236 of the first parallelogrammic link mechanism 16, that is, on the central axis of the first parallelogrammic link mechanism 16. Thereupon, both the gravity W and a reaction force F of the first gas spring 236 act in the vertical direction.

Even if the gravity W and the reaction force F of the first gas spring 236 are not equal, therefore, a force generated by their difference acts only on the first and second arms 228a and 228b. Thus, weight moments that act on the second rotating shaft $X_2$ and the fifth rotating shaft $X_5$ are balanced with each other, so that the first parallelogrammic link mechanism 16 itself is kept as it is.

If the lens barrel portion 22 is then forced to move, the first parallelogrammic link mechanism 16 is brought to a deformed state, as shown in FIG. 10B, for example. If the angle of the axial direction of the first and second arms 228a and 228b and the first gas spring 236 to a horizontal plane is α, in this state, the gravity W and the reaction force F are given by $$W = F \sin \alpha.$$

In other words, the above relational expression is always fulfilled by the reaction force F, a variable that changes with respect to the gravity W as a constant as the first parallelogrammic link mechanism 16 is deformed, and the angle α of the axial direction of the first gas spring 236 to the horizontal plane. Accordingly, the first parallelogrammic link mechanism 16 is balanced and kept as it is even after the deformation. Thus, the first parallelogrammic link mechanism 16 is balanced and rests in a deformed state.

Specifically, the variation of the reaction force F of the first gas spring 236 can be set in accordance with the equipment length, spring constant, etc. of the first gas spring 236. The variation of the angle α can be set based on the location of the rotating shafts $X_2$, $X_3$, $X_4$, $X_5$, $X_6$ and $A_{14}$.

The angle α is an acute angle in FIG. 10B. If it is an blunt angle, however, the same state for the acute angle can be maintained after the deformation provided that the sign, positive or negative, of the angular moments that act on the rotating shafts $X_2$ and $X_5$ is inverted. Thus, the first parallelogrammic link mechanism 16 is balanced and rests in a deformed state without regard to the acuteness or bluntness of the angle α.

As shown in FIG. 9A, the L-shaped joint 18 is provided with the second parallelogrammic link mechanism 20. The second parallelogrammic link mechanism 20 includes third and fourth arms 228c and 228d and a second gas spring 240 as a compression spring.

One end portion of the third arm 228c is connected to the other end portion or the upper end portion of L-shaped joint 18 by a seventh rotating shaft $X_7$ (second horizontal rotating shaft). The lens barrel portion 22 is located on the other end portion of the third arm 228c.

The lens barrel portion 22 is provided with a lens barrel 22b, L-shaped link 22c, rotating seat 22d, and arm 22e. The other end portion of the third arm 228c is connected to a bent portion of the L-shaped link 22c by an eighth rotating shaft $X_8$.

One end portion of the second gas spring 240 is connected to the L-shaped joint 18 by a ninth rotating shaft $X_9$. The other end portion of the second gas spring 240 is connected to the third arm 228c by a tenth rotating shaft $X_{10}$. The tenth rotating shaft $X_{10}$ is located between the seventh and eighth rotating shafts $X_7$ and $X_8$.

The fourth arm 228d is formed substantially in the shape of a cylinder such that it can contain the third arm 228c and the second gas spring 240. One end portion of the fourth arm 228d is connected to the L-shaped joint 18 by an eleventh rotating shaft $X_{11}$ (second horizontal rotating shaft). The eleventh rotating shaft $X_{11}$ is located between the seventh and ninth rotating shafts $X_7$ and $X_9$.

The other end portion of the fourth arm 228d is connected to one end portion (lower end portion) of the L-shaped link 22c by a twelfth rotating shaft $X_{12}$. Specifically, the fourth arm 228d is supported on the joint 18 and the L-shaped link 22c of the lens barrel portion 22 by the eleventh and twelfth rotating shafts $X_{11}$ and $X_{12}$.

Thus, the third and fourth arms 228c and 228d, the second gas spring 240, the L-shaped joint 18, the L-shaped link 22c, the rotating shafts $X_7$, $X_9$ and $X_{11}$ of the L-shaped joint 18, and the rotating shafts $X_8$ and $X_{12}$ of the L-shaped link 22c constitute the vertical motion arm of the lens barrel portion 22 as the second parallelogrammic link mechanism 20.

The other end portion of the L-shaped link 22c projects outward from the other end portion of the fourth arm 228d. The lower end portion of the rotating seat 22d is supported on the other end portion of the L-shaped link 22c for rotation around a thirteenth rotating shaft (vertical shaft) $X_{13}$. The lower end portion of the arm 22e is attached to the upper end portion of the rotating seat 22d. The lens barrel 22b is mounted on the upper end portion of the arm 22e. Here the lens barrel portion 22 is located so that a midpoint between two observing eyes 300 of an observer is positioned on an extension of the vertical shaft $X_{13}$.

The weight of each component member of the second parallelogrammic link mechanism 20 is regarded as negligible. Thus, the second gas spring 240 acts so as to cancel angular moments around the rotating shafts $X_7$ and $X_9$ that are generated by the lens barrel portion 22, a heavy object, on the L-shaped link 22c. In this case, the second parallelogrammic link mechanism 20 is a closed system that can be balanced independently. Thus, weight moments that act on the seventh rotating shaft $X_7$ and the eleventh rotating shaft $X_{11}$ are balanced with each other, so that the second parallelogrammic link mechanism 20 itself is kept as it is. Accordingly, the second parallelogrammic link mechanism 20 is balanced and rests in a deformed state.

The following is a description of the function of the operating microscope 10 according to this embodiment.

Figure 11A:
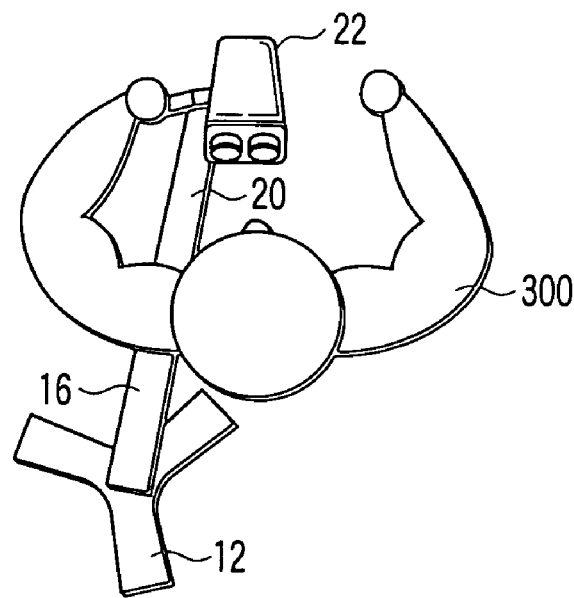
FIG. 11A is a schematic plan view illustrating a state in which the operating microscope according to the fifth embodiment is used.
Figure 11B:
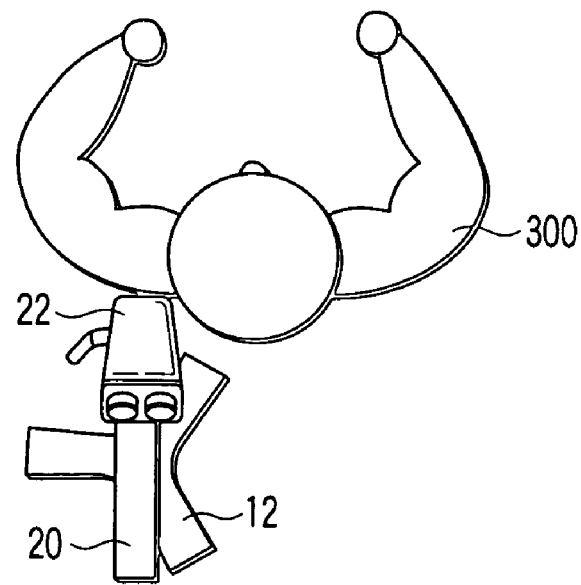
FIG. 11B is a schematic plan view illustrating a state in which the operating microscope according to the fifth embodiment is used.

FIGS. 11A and 11B illustrate states in which the operating microscope 10 according to this embodiment is used. As the lens barrel portion 22 is moved in the vertical or horizontal direction from the state shown in FIG. 11A to the state shown in FIG. 11B, the first and second parallelogrammic link mechanisms 16 and 18 are prevented from moving in the lateral direction of an operator 300 to widen a space for the operator 300. Thus, the operating microscope 10 can be used in a space-saving manner by the operator 300.

In performing a surgical operation, the lens barrel portion 22 of the operating microscope 10 set on the level floor surface shown in FIG. 9A may be moved in the left-right direction (left-right direction of the drawing plane of FIG. 9A). In doing this, the operator 300 holds the arm 22e of the lens barrel portion 22 and moves the lens barrel portion 22 in the left-right direction.

In the first parallelogrammic link mechanism 16, the third rotating shaft $X_3$ of the first arm 228a and the sixth rotating shaft $X_6$ of the second arm 228b move to positions of rotating shafts $X_3'$ and $X_6'$ or rotating shafts $X_3''$ and $X_6''$, respectively. As this is done, the first parallelogrammic link mechanism 16 is deformed in a manner such that it is balanced by the agency of the first gas spring 236. Thus, the lens barrel portion 22 moves together with the lens barrel portion 22 on the L-shaped link 22c in a circular arc.

In performing a surgical operation, the lens barrel portion 22 of the operating microscope 10 set on the level floor surface shown in FIG. 9A may be moved in the up-down direction (up-down direction of the drawing plane of FIG. 9A). In doing this, the operator 300 holds the arm 22e of the lens barrel portion 22 and moves the lens barrel portion 22 in the up-down direction.

In the second parallelogrammic link mechanism 20, the eighth rotating shaft $X_8$ of the third arm 228c and the twelfth rotating shaft $X_{12}$ of the second arm 228b move to positions of rotating shafts $X_8'$ and $X_{12}'$ or rotating shafts $X_8''$ and $X_{12}''$, respectively. As this is done, the second parallelogrammic link mechanism 20 is deformed in a manner such that it is balanced by the agency of the second gas spring 240. Thus, the lens barrel portion 22 moves together with the lens barrel portion 22 on the L-shaped link 22c in a circular arc.

When these two circular-arc movements are combined together, therefore, the lens barrel portion 22 can move in all directions. As this is done, the first parallelogrammic link mechanism 16 is balanced by the first gas spring 236, while the second parallelogrammic link mechanism 20 is balanced by the second gas spring 240. Thus, the lens barrel portion 22 is balanced and rests in any posture.

The following is a description of a case where the operating microscope 10 according to this embodiment is located on an inclined floor surface.

As in the first embodiment, the operating microscope 10 is located on the floor surface that is inclined at the tilt angle $\theta_Z$ so that its front (on the side of the lens barrel portion 22) and back are on the higher and lower sides, respectively, for example.

In the first state, the base 12 is inclined with the first and second arms 228a and 228b kept in the vertical direction. Alternatively, the first and second arms 228a and 228b are inclined at the tilt angle $\theta_Z$.

While the gravity W produced by the lens barrel portion 22 is applied to the central axis (first gas spring 236) of the first parallelogrammic link mechanism 16, which is a closed system, gravities that act individually on the first and second arms 228a and 228b vary from each other, owing to the inclination of the base 12 and the inclinations of the first and second arms 228a and 228b. Thus, an angular moment is generated around the fourth rotating shaft $X_4$ at the lower end portion of the first gas spring 236.

Thereupon, the first parallelogrammic link mechanism 16 shown in FIG. 10A starts to be disbalanced and deformed. The first and second arms 228a and 228b tilt backward (or away from the lens barrel portion 22) around the fourth rotating shaft $X_4$, and the lens barrel portion 22 also naturally moves backward.

In order to correct the imbalance that is attributable to the inclination of the floor, the slider 52 shown in FIG. 9B is moved for an appropriate movement amount with respect to the axis of the first gas spring 236 shown in FIG. 10A. Thereupon, the rotating shaft $A_{14}$ of the floor tilt correcting mechanism 44 is located in a position reached when it is rocked around the fourth rotating shaft $X_4$ for an angle equal to the tilt angle of the floor surface. Thus, a moment to cancel the aforesaid angular moment acts around the fourth rotating shaft $X_4$ at the lower end portion of the first gas spring 236.

Accordingly, the first parallelogrammic link mechanism 16 rests with the angular moment balanced as the rotating shaft $A_{14}$ of the floor tilt correcting mechanism 44 is moved. Thus, the lens barrel portion 22 is balanced and rests.

In actual adjustment operation, the movement amount of the rotating shaft $A_{14}$ of the floor tilt correcting mechanism 44 need not be precisely calculated, and it is determined whether the first and second arms 228a and 228b of the first parallelogrammic link mechanism 16 tilt backward or forward with respect to the arm seat 14. If the first and second arms 228a and 228b tilt backward, the rotary knob 60 of the floor tilt correcting mechanism 44 should only be rotated counterclockwise so that the first and second arms 228a and 228b rest. If the first and second arms 228a and 228b tilt forward, the rotary knob 60 should only be rotated clockwise in like manner.

According to this embodiment, as described above, the following effect can be obtained.

The first gas spring 236 that serves as a compression spring free from buckling is located on the central axis of the first parallelogrammic link mechanism 16 so as to be interposed between the L-shaped joint 18 and the arm seat 14. Thus, reversible weight moments around the second and fifth rotating shafts $X_2$ and $X_5$ of the first parallelogrammic link mechanism 16 can be canceled by only interposing the first gas spring 236 in this manner. Therefore, the operating microscope 10 can be made small-sized.

Since the second arm 228b of the first parallelogrammic link mechanism 16 is configured to contain the first arm 228a and the first gas spring 236 therein, relatively moving members can be prevented from being exposed to the outside. Thus, the first arm 228a and the first gas spring 236 can be prevented from being run against their peripheral objects.

Since the first and second parallelogrammic link mechanisms 16 and 20 are formed as independent systems, moreover, they can be individually balanced with each other. Even if the floor surface is inclined, in particular, generation of a moment caused by the inclination of the floor surface can be corrected merely by locating the floor tilt correcting mechanism 44 in the first parallelogrammic link mechanism 16 and performing a simple operation.

Since the first and second parallelogrammic link mechanisms 16 and 20 are prevented from projecting laterally from the operator 300, furthermore, the operation space for the operating microscope 10 can be reduced. The same effect can be also obtained with the foregoing first to fourth embodiments.

A sixth embodiment will now be described with reference to FIG. 12. This embodiment is a modification of the operating microscope 10 according to the fifth embodiment, so that like numerals are used to designate the same members as those described in connection with the fifth embodiment, and a detailed description of those members is omitted.

Figure 12:
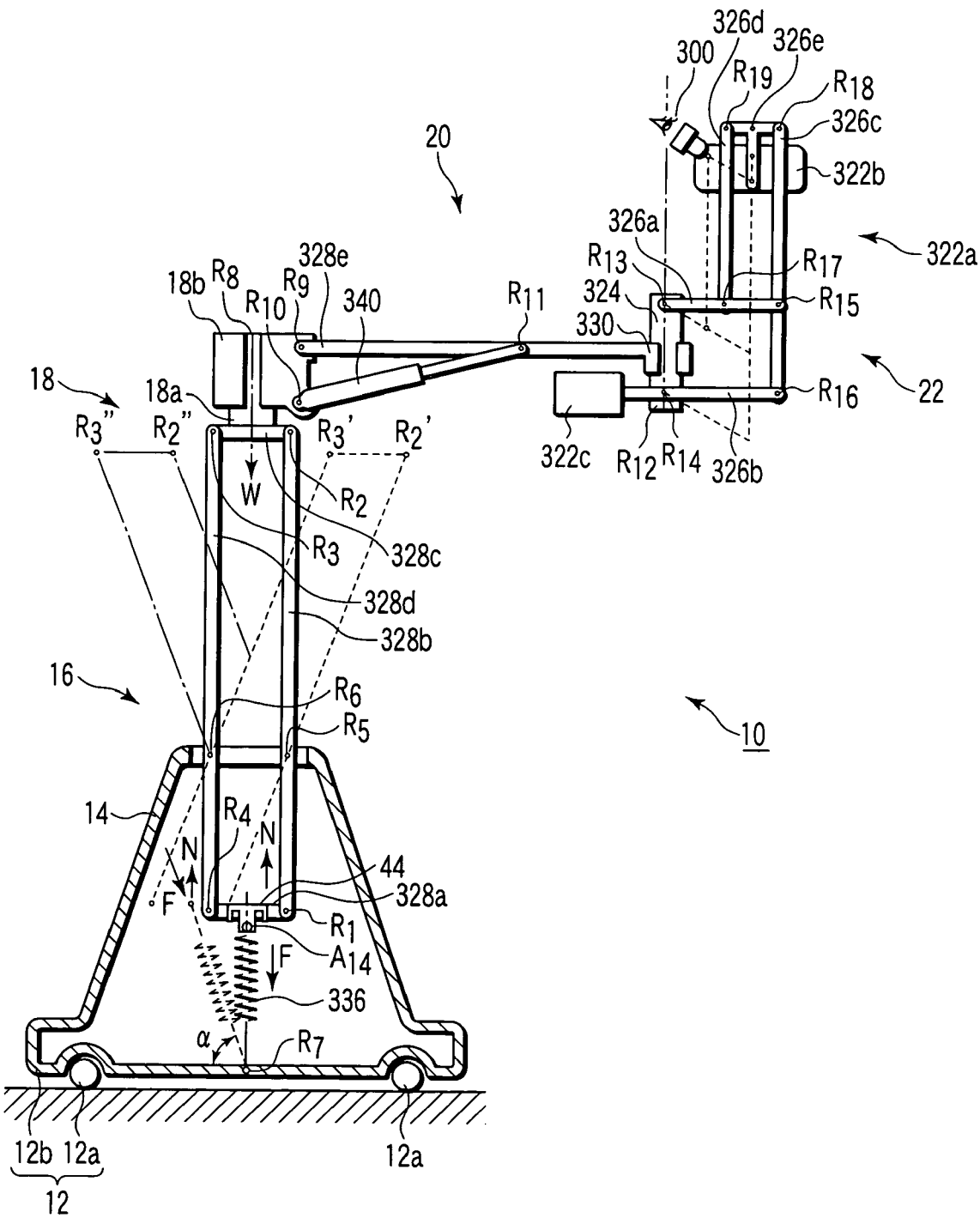
FIG. 12 is a schematic front view, partially in section, showing an operating microscope according to a sixth embodiment.

As shown in FIG. 12, the operating microscope 10 according to this embodiment includes the base 12, post 14, first parallelogrammic link mechanism (horizontal motion arm) 16, joint 18, vertical motion arm 20, and lens barrel portion 22.

The base 12 is formed integrally with the post 14. The post 14 is provided with a tension coil spring 336 for use as a first gas spring.

The first parallelogrammic link mechanism 16 is provided with first to fourth links 328a, 328b, 328c and 328d. The first and second links 328a and 328b are connected to each other by a first rotating shaft $R_1$. The second and third links 328b and 328c are connected to each other by a second rotating shaft $R_2$. The third and fourth links 328c and 328d are connected to each other by a third rotating shaft $R_3$. The first and fourth links 328a and 328d are connected to each other by a fourth rotating shaft $R_4$.

The second and fourth links 328b and 328d are supported on the post 14 by fifth and sixth rotating shafts $R_5$ and $R_6$ (first horizontal rotating shafts). Among the links, the first link 328a is provided with a floor tilt correcting mechanism 44. This floor tilt correcting mechanism 44, like the one according to the fifth embodiment, may be either mounted on the first link 328a or formed as a part of the first link 328a.

The tension coil spring 336 is located between the base 12 and the first link 328a. The upper end portion of the coil spring 336 is connected to the rotating shaft $A_{14}$ of the floor tilt correcting mechanism 44 of the first link 328a. On the other hand, the lower end portion of the coil spring 336 is connected to a seventh rotating shaft $R_7$ (second fulcrum) in the base 12 that is integral with the post 14.

Thus, in this embodiment, the first parallelogrammic link mechanism 16 and the tension coil spring 336 constitute a horizontal motion arm.

The joint 18 is located on the third link 328c of the first parallelogrammic link mechanism 16. The joint 18 is provided with a rotating seat 18a and an arm seat 18b.

The rotating seat 18a is mounted on the top of the central part of the third link 328c. The arm seat 18b is connected to the rotating seat 18a. The arm seat 18b is rotatable around an eighth rotating shaft $R_8$ with respect to the rotating seat 18a.

One end portion of the vertical motion arm 20 is located on the arm seat 18b. The vertical motion arm 20 is provided with a fifth link 328e and a gas spring 340.

One end portion of the fifth link 328e is connected to the upper end portion of the arm seat 18b by a ninth rotating shaft $R_9$ (second horizontal rotating shaft). One end portion of the gas spring 340 is connected to the lower end portion of the arm seat 18b by a tenth rotating shaft $R_{10}$. The other end portion of the gas spring 340 is connected to an eleventh rotating shaft $R_{10}$ between the one end portion and the other end portion of the fifth link 328e. Further, a bearing portion 330 is formed on the other end portion of the fifth link 328e.

Thus, the fifth link 328e and the gas spring 340 form the vertical motion arm 20.

The lens barrel portion 22 is located on the other end portion of the vertical motion arm 20.

The lens barrel portion 22 is provided with a parallel link mechanism 322a, a lens barrel 322b, and a counterweight 322c.

The parallel link mechanism 322a is provided with a vertical shaft 324 and first to fifth links 326a, 326b, 326c, 326d and 326e.

The vertical shaft 324 is located on the bearing portion 330 at the other end portion of the fifth link 328e. The vertical shaft 324 is rotatable around a vertical twelfth rotating shaft $R_{12}$.

One end portion of the fifth link 326a is connected to the upper end portion of the vertical shaft 324 by a thirteenth rotating shaft $R_{13}$. The second link 326b is connected to the lower end portion of the vertical shaft 324 by a fourteenth rotating shaft $R_{14}$. The counterweight 322c for balancing with the lens barrel 322b is located on one end portion of the second link 326b. The third link 326c is connected to the respective other end portions of the first and second links 326a and 326b by fifteenth and sixteenth rotating shafts $R_{15}$ and $R_{16}$, respectively.

The first link 326a is further provided with a seventeenth rotating shaft $R_{17}$. The lower end portion of the fourth link 326d is connected to the seventeenth rotating shaft $R_{17}$.

Eighteenth and nineteenth rotating shafts $R_{18}$ and $R_{19}$ are located on the respective upper end portions of the third and fourth links 326c and 326d, respectively. The fifth link 326e is connected between the eighteenth and nineteenth rotating shafts $R_{18}$ and $R_{19}$. The fifth link 326e is provided with the lens barrel 322b. The line of sight of the operator 300 is located on the lens barrel 322b so as to be on the same axis with the vertical shaft 324. Thus, the lens barrel 322b is located so that a midpoint between the two eyes of the observer 300 is positioned on the axis of the vertical shaft 324.

The following is a description of the function of the operating microscope 10 according to this embodiment.

When the first parallelogrammic link mechanism 16 is in the state shown in FIG. 12, that is, when the first to fourth rotating shafts $R_1$, $R_2$, $R_3$ and $R_4$ are just located individually on the vertexes of a rectangle, the weight W that is applied to the first parallelogrammic link mechanism 16 by the lens barrel portion 22 and the reaction force F of the tension coil spring 336 both act in the vertical direction. As in the case of the fifth embodiment, therefore, weight moments and angular moments that act on the rotating shafts $R_5$ and $R_6$ are balanced, so that the first parallelogrammic link mechanism 16 itself is kept as it is.

If the lens barrel portion 22 is then forced to move, the first parallelogrammic link mechanism 16 is deformed into a state indicated by broken line in FIG. 12. If the angle of the tension coil spring 336 to a horizontal plane and a force that is applied to the opposite side around the rotating shafts $R_5$ and $R_6$ by the weight W are α and N, in this state, the force N and the reaction force F are given by $$N = F \sin \alpha.$$

In other words, the state is kept as it is even after the deformation, as in the fifth embodiment.

The following is a description of the function of the gas spring 340. The gas spring 340 serves to cancel an angular moment around the ninth rotating shaft $R_9$ that is generated by a heavy object such as the lens barrel portion 22.

When the observer 300 shown in FIG. 12 moves his/her field of vision in a direction perpendicular to the drawing plane, the observer 300 holds the lens barrel portion 22 and applies a force in an appropriate direction to it. Thereupon, the vertical shaft 324 of the parallel link mechanism 322a of the lens barrel portion 22 rocks around the twelfth rotating shaft $R_{12}$ with respect to the bearing portion 330 of the fifth link 328e of the vertical motion arm 20. Thus, the lens barrel portion 22 can rock around the vertical shaft 324 to move the field of vision.

When the observer 300 shown in FIG. 12 moves his/her field of vision in the vertical direction of the drawing plane, the observer 300 holds the lens barrel portion 22 and applies a force in an appropriate direction to it. Thereupon, the parallel link mechanism 322a of the lens barrel portion 22 is deformed, as indicated by a broken line. Thus, the lens barrel portion 22 can tilt around the observer's eyes, thereby moving the field of vision. As this is done, the lens barrel portion 22 is balanced by the counterweight 322c. Specifically, the counterweight 322c moves in association with the inclination of the lens barrel 322b that is caused by the vertical movement of the field of vision, thus acting to cancel the angular moment with respect to all tilt angle of the lens barrel 322b.

As shown in FIG. 12, the lens barrel portion 22 is moved in a direction perpendicular to the drawing plane. If the observer 300 holds the lens barrel portion 22 and applies a force in an appropriate direction to it, the arm seat 18b rocks around the eighth rotating shaft $R_8$ with respect to the rotating seat 18a that is connected to the first parallelogrammic link mechanism 16. Thus, the lens barrel portion 22 moves together with the vertical motion arm 20 in a circular arc.

In performing a surgical operation, the lens barrel portion 22 of the operating microscope 10 set on the level floor surface shown in FIG. 12 may be moved in the left-right direction (left-right direction of the drawing plane of FIG. 12). In doing this, the operator 300 holds the parallel link mechanism 322a of the lens barrel portion 22 and moves the lens barrel portion 22 in the left-right direction.

In the first parallelogrammic link mechanism 16, the fifth rotating shaft $R_5$ of the second link 328b and the sixth rotating shaft $R_6$ of the fourth arm 228d move to positions of rotating shafts $R_5'$ and $R_6'$ or rotating shafts $R_5''$ and $R_6''$, respectively. As this is done, the first parallelogrammic link mechanism 16 is deformed in a manner such that it is balanced by the agency of the tension coil spring 336. Thus, the lens barrel portion 22 moves in a circular arc.

In performing a surgical operation, the lens barrel portion 22 of the operating microscope 10 set on the level floor surface shown in FIG. 12 may be moved in the up-down direction (up-down direction of the drawing plane of FIG. 12). In doing this, the operator 300 holds the parallel link mechanism 322a of the lens barrel portion 22 and moves the lens barrel portion 22 in the up-down direction.

In the parallel link mechanism 322a, the twelfth rotating shaft $R_{12}$ of the vertical shaft 324 and the thirteenth rotating shaft $R_{13}$ move to positions of rotating shafts $R_{12}'$ and $R_{13}'$ or rotating shafts $R_{12}''$ and $R_{13}''$, respectively. As this is done, the parallel link mechanism 322a of the lens barrel portion 22 is deformed in a manner such that it is balanced by the agency of the gas spring 340. Thus, the lens barrel portion 22 moves in a circular arc.

When these two circular-arc movements are combined together, therefore, the lens barrel portion 22 can move in all directions. As this is done, the first parallelogrammic link mechanism 16 is balanced by the tension coil spring 336, while the parallel link mechanism 322a of the lens barrel portion 22 is balanced by the gas spring 340. Thus, the lens barrel portion 22 is balanced and rests in any posture.

The following is a description of a case where the operating microscope 10 according to this embodiment is located on an inclined floor surface.

As in the first embodiment, the operating microscope 10 is located on the floor surface that is inclined at the tilt angle $\theta_Z$ so that its front (on the side of the lens barrel portion 22) and back are on the higher and lower sides, respectively, for example.

In the first state, the base 12 is inclined with the second and fourth arms 328b and 328d kept in the vertical direction. Alternatively, the second and fourth arms 328b and 328d are inclined at the tilt angle $\theta_Z$.

While the gravity W produced by the lens barrel portion 22 is applied to the central axis (first gas spring 336) of the first parallelogrammic link mechanism 16, which is a closed system, gravities that act individually on the second and fourth arms 328b and 328d vary from each other, owing to the inclination of the base 12. Thus, an angular moment is generated around the seventh rotating shaft $R_7$ at the lower end portion of the first gas spring 336.

Thereupon, the first parallelogrammic link mechanism 16 starts to be disbalanced and deformed. The second and fourth arms 328b and 328d tilt backward (or away from the lens barrel portion 22) around the seventh rotating shaft $R_7$, and the lens barrel portion 22 also naturally moves backward.

In order to correct the imbalance that is attributable to the inclination of the floor, the slider 52 shown in FIG. 9B is moved for an appropriate movement amount with respect to the axis of the first gas spring 336. Thereupon, the rotating shaft $A_{14}$ of the floor tilt correcting mechanism 44 is located in a position reached when it is rocked around the seventh rotating shaft $R_7$ for an angle equal to the tilt angle of the floor surface. Thus, a moment to cancel the aforesaid angular moment acts around the seventh rotating shaft $R_7$ at the lower end portion of the first gas spring 336.

Accordingly, the first parallelogrammic link mechanism 16 rests with the angular moment balanced as the rotating shaft $A_{14}$ of the floor tilt correcting mechanism 44 is moved. Thus, the lens barrel portion 22 is balanced and rests.

In actual adjustment operation, the movement amount of the rotating shaft $A_{14}$ of the floor tilt correcting mechanism 44 need not be precisely calculated, and it is determined whether the second and fourth arms 328b and 328d of the first parallelogrammic link mechanism 16 tilt backward or forward with respect to the base 12. If the second and fourth arms 328b and 328d tilt backward, the rotary knob 60 of the floor tilt correcting mechanism 44 should only be rotated counterclockwise so that the second and fourth arms 328b and 328d rest. If the second and fourth arms 328b and 328d tilt forward, the rotary knob 60 should only be rotated clockwise in like manner.

According to this embodiment, as described above, the following effect can be obtained.

The vertical movement of the field of vision as in the drawing plane of FIG. 12 can be made by deforming the parallel link mechanism 322a of the lens barrel portion 22 to move the lens barrel portion 22 around the observer's eyes. Further, the movement of the field of vision perpendicular to the drawing plane of FIG. 12 can be made by allowing the parallel link mechanism 322a of the lens barrel portion 22 to rock around the twelfth rotating shaft $R_{12}$ so that the lens barrel portion 22 moves around a midpoint between the observer's eyes. Thus, the shift of the positions of the observer's eyes can be minimized. Since the angular moment of the lens barrel portion 22 is canceled by the counterweight 322c, moreover, the motion is so light that the field of vision can be moved even if a force is applied to the lens barrel portion 22 by a contact part of the observer 300, e.g., the forehead of the observer.

In the first parallelogrammic link mechanism 16 based on the use of the tension coil spring 336, the reversible weight moments around the rotating shafts $R_5$ and $R_6$ are canceled merely by interposing the tension coil spring 336 between the base 12 and the first arm 328a of the first parallelogrammic link mechanism 16, so that a simple structure can be formed at low cost.

Although several embodiments have been described specifically with reference to the drawing, this invention is not limited to the foregoing embodiments but includes all workings carried out without departing from its spirit.

What is claimed is:

1. An operating microscope comprising:
   a base set on a floor surface;
   a post held for rotation around a vertical rotation axis with respect to the base;
   a horizontal motion arm held for rotation around a first horizontal rotation axis with respect to the post;
   a vertical motion arm held for rotation around a second horizontal rotation axis with respect to the horizontal motion arm;
   a lens barrel portion supported by the vertical motion arm;
   an elastic member which is axially expandable and contractable and which is provided between the post and the horizontal motion arm and cancels an angular moment around the horizontal motion arm;
   a fulcrum which is provided on the horizontal motion arm and receives a force from an end of the elastic member; and
   a floor tilt correcting mechanism configured to shift the position of the fulcrum in a direction substantially perpendicular to a longitudinal direction of the horizontal motion arm and in a direction substantially perpendicular to the first horizontal rotation axis.

2. The operating microscope according to claim 1, further comprising a tilt angle detecting mechanism which detects a tilt angle of the floor surface on which the base is set.

3. An operating microscope comprising:
   a base set on a floor surface;
   a post held for rotation around a vertical rotation axis with respect to the base;
   a horizontal motion arm held for rotation around a first horizontal rotation axis with respect to the post;
   a vertical motion arm held for rotation around a second horizontal rotation axis with respect to the horizontal motion arm;
   a lens barrel portion supported by the vertical motion arm;
   an elastic member which is provided between the post and the horizontal motion arm and cancels an angular moment around the horizontal motion arm;
   a fulcrum which is provided on the horizontal motion arm and receives a force from the elastic member;
   a fulcrum moving mechanism configured to shift the position of the fulcrum in a direction substantially perpendicular to a longitudinal direction of the horizontal motion arm; and
   a tilt angle detecting mechanism which detects a tilt angle of the floor surface on which the base is set.

4. The operating microscope according to claim 3, wherein the tilt angle detecting mechanism is configured to detect the tilt angle of the floor surface in a direction perpendicular to the first horizontal rotation axis.

5. The operating microscope according to claim 3, wherein the tilt angle detecting mechanism includes a movement control mechanism which moves the fulcrum moving mechanism based on a result of the detection.

6. The operating microscope according to claim 3, wherein the tilt angle detecting mechanism includes a tilt angle display mechanism which displays the tilt angle of the floor surface.

7. The operating microscope according to claim 3, wherein the tilt angle detecting mechanism is provided on the post.

* * * * *